United States Patent
Shimizu et al.

(10) Patent No.: US 6,306,898 B1
(45) Date of Patent: *Oct. 23, 2001

(54) EXTERNAL PREPARATIONS FOR THE TREATMENT OF DERMATOSES

(75) Inventors: Tatsuo Shimizu; Tomoko Horiguchi; Kiyoshi Kuriyama; Mitsuo Watabe, all of Osaka (JP)

(73) Assignee: Sekisui Kaisha Kogyo Kabushiki Kaisha, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/457,368

(22) Filed: Dec. 9, 1999

Related U.S. Application Data

(63) Continuation of application No. 08/750,993, filed on Apr. 1, 1997.

(30) Foreign Application Priority Data

| Apr. 21, 1995 | (JP) | 7-96911 |
| Aug. 8, 1995 | (JP) | 7-202232 |
| Oct. 18, 1995 | (JP) | 7-270089 |
| Oct. 18, 1995 | (JP) | 7-270090 |
| Oct. 18, 1995 | (JP) | 7-270093 |

(51) Int. Cl.⁷ .......... A61K 31/355; A61K 31/01
(52) U.S. Cl. .......... 514/458; 514/763
(58) Field of Search .......... 514/458, 762, 514/861, 863, 864, 763

(56) References Cited

U.S. PATENT DOCUMENTS

| 4,216,201 | 8/1980 | Calvo | 424/63 |
| 4,454,159 | 6/1984 | Musher | 424/358 |
| 4,981,681 | 1/1991 | Tosti | 424/78 |
| 5,378,461 | 1/1995 | Neigut | 424/94.1 |

FOREIGN PATENT DOCUMENTS

| 35 35 084 A1 | 4/1987 | (DE) . |
| 0 100 459 A2 | 2/1984 | (EP) . |
| 0 127 536 A1 | 12/1984 | (EP) . |
| 0 313 303 A2 | 4/1989 | (EP) . |
| 0 539 215 A1 | 4/1993 | (EP) . |
| 51-101139 | 9/1976 | (JP) . |
| 53-34912 | 3/1978 | (JP) . |
| 58-183631 | 10/1983 | (JP) . |
| 62-87509 | 4/1987 | (JP) . |
| 63-126542 | 5/1988 | (JP) . |
| 4-82834 | 3/1992 | (JP) . |
| 4-82835 | 3/1992 | (JP) . |
| 4-169525 | 6/1992 | (JP) . |
| 5-269214 | 10/1993 | (JP) . |
| 6-40858 | 2/1994 | (JP) . |
| 6-128136 | 5/1994 | (JP) . |
| 6-172123 | 6/1994 | (JP) . |
| 6-172165 | 6/1994 | (JP) . |
| 6-179619 | 6/1994 | (JP) . |
| 1751198 A1 | 7/1992 | (SU) . |
| WO 95/06482 | 3/1995 | (WO) . |

OTHER PUBLICATIONS

Database WPI, Section Ch, Week 199440, XP002138143 and JP 06–247852, Sep. 6, 1994, abstract.
Patent Abstracts of Japan, vol. 014, No. 068, Feb. 8, 1990 and JP 01–290613 A, Nov. 22, 1989, abstract.
Database WPI, Section Ch, Week 199303, XP002138144 and JP 04–346917 A, Dec. 2, 1992, abstract.

*Primary Examiner*—William R. A. Jarvis
*Assistant Examiner*—Vickie Kim
(74) *Attorney, Agent, or Firm*—Connlloy Bove Lodge & Hutz

(57) ABSTRACT

The first invention provides an external preparation for treating dermatoses comprising vitamin E and squalane, which has an efficacy at least equivalent to that of external preparations containing adrenocortical hormones as the active ingredient. The second invention provides an external preparation for treating dermatoses comprising an adrenocortical hormone, vitamin E and squalane, which is reduced in adrenocortical hormone content as compared with conventional preparations, is also reduced in side effects, and has high clinical efficacy. The third invention provides an external preparation for treating dermatoses comprising a nonsteroidal antiinflammatory agent, vitamin E and squalane and/or squalene, which is reduced in side effects and is highly efficacious. The fourth invention provides an external preparation for treating dermatoses comprising an antihistaminic agent, vitamin E and squalane and/or squalene, which is reduced in side effects and is highly efficacious like the above preparation. The fifth invention provides an external preparation for treating dermatoses comprising vitamin E, squalene and squalane, which is reduced in side effects and is highly efficacious.

2 Claims, No Drawings

EXTERNAL PREPARATIONS FOR THE TREATMENT OF DERMATOSES

CROSS REFERENCE TO RELATED APPLICATION

This application is a continuation of U.S. patent application Ser. No. 08/750,993 filed Apr. 1, 1997 which application is the national phase of PCT/JP96/01081 filed Apr. 22, 1996.

TECHNICAL FIELD

The present invention relates to external preparations for the treatment of dermatoses.

BACKGROUND ART

External preparations containing an adrenocortical hormone have so far been used widely in the treatment of dermatoses, in particular intractable dermatoses such as a topic dermatitis and contact dermatitis and it is known that they have high pharmacological effects (Gekkan Yakuji (Pharmaceuticals Monthly); 26, 8, 55, 1984). Japanese Kokai Publication Sho-62-149620, for instance, discloses an external preparation containing an adrenocortical hormone as a principal active component.

However, adrenocortial hormone-containing external preparations may possibly induce adverse effects at the sites of application, for example increased easy infectivity, skin thinning, vascular wall embrittlement and abnormal activation of the pilosebaceous system and, in addition, the drug substances endermically absorbed may possibly produce systemic adverse effects. Thus, the closest attention should be paid to their doses. Therefore, for hydrocortisone acetate, for instance, which is a typical adrenocortical hormone, the Japanese Pharmacopoeia prescribes an upper limit use concentration of about 1% by weight and, for dexamethasone and prednisolone, an upper limit concentration of about 0.1 to 0.5% by weight.

On the other hand, external preparations with reduced adverse effects are also available, for example external preparations containing a nonsteroidal antiinflammatory agent and/or an antihistaminic agent. However, as compared with adrenocortical hormone-containing ones, they are much less effective against such intractable dermatoses as mentioned above (Shinyaku to Chiryo (New Remedies and Therapy); 25, 298, 41, 1984).

As mentioned above, adrenocortical hormones have high pharmacological effects but are disadvantageous in that they have strong side effects. Therefore, it is earnestly desired that preparations with which clinical effects comparable to those attained with the conventional preparations can be produced at lower adrenocortical hormone concentrations be developed. In the state of the art, even if higher clinical effects are required, it is impossible to increase their contents to levels exceeding those currently employed, when their side effects are taken into consideration.

For solving these problems, Japanese Kokai Publication Sho-61-40210 discloses a preparation for treating dermatoses and skin protection which comprises vitamin E and Japanese Kokai Publication Sho-53-136521 discloses a preparation for the treatment of vegetating dermatoses which contains α-tocopherol. However, these are insufficiently effective in intractable dermatoses possibly due to the low concentration of vitamin E or α-tocopherol in the preparations.

Japanese Kokai Publication Hei-06-179619 discloses an external preparation for the treatment of dermatoses which contains vitamin E and a transdermal absorption enhancer. However, when it is administered continuedly for achieving satisfactory therapeutic effects, the transdermal absorption enhancer may possibly produce skin irritating effects.

Furthermore, Japanese Kokai Publication Hei-06-247852 discloses an external preparation for the treatment of dermatoses which contains 1 to 30% by weight of vitamin E and 1 to 30% by weight of squalene. It is known that this vitamin E- and squalene-containing external preparation for treating dermatoses can be widely applied to dermatoses without producing such adverse effects as encountered with the steroid-containing preparations mentioned above. However, for producing higher clinical effects, preparations showing still stronger effects are desired.

SUMMARY OF THE INVENTION

In a first aspect of the present invention, it is an object thereof to provide an external preparation for the treatment of dermatoses which has an efficacy at least equivalent to that of external preparations containing an adrenocortical hormone as an active ingredient and which produces only reduced adverse effects. In the first aspect thereof, the present invention provides an external preparation for the treatment of dermatoses which comprises vitamin E and squalane.

In a second aspect, it is an object of the present invention to provide an external preparation for the treatment of dermatoses in which the adrenocortical hormone content is lower as compared with conventional preparations and which can produce high clinical efficacy with reduced side effects. In the second aspect thereof, the present invention provides an external preparation for the treatment of dermatoses which comprises an adrenocortical hormone, vitamin E and squalane.

In a third aspect, it is an object of the present invention to provide an external preparation for the treatment of dermatoses which is highly efficacious but reduced in side effects. In this third aspect, the present invention provides an external preparation for the treatment of dermatoses which comprises a nonsteroidal antiinflammatory agent, vitamin E and squalane and/or squalene.

In a fourth aspect, it is an object of the present invention to provide an external preparation for the treatment of dermatoses which is highly efficacious but reduced in side effects. In this fourth aspect, the present invention provides an external preparation for the treatment of dermatoses which comprises an antihistaminic agent, vitamin E and squalane and/or squalene.

In a fifth aspect, it is an object of the present invention to provide an external preparation for the treatment of dermatoses which is highly efficacious but reduced in side effects. In the fifth aspect, the present invention provides an external preparation for the treatment of dermatoses which comprises vitamin E, squalene and squalane.

DETAILED DISCLOSURE OF THE INVENTION

First, the present invention is described in detail in its first aspect.

The external preparation for the treatment of dermatoses according to the first aspect of the present invention comprises vitamin E and squalane.

The term "vitamin E" as used herein includes tocopherol (vitamin E) and derivatives thereof and, as examples thereof as listed in the Japanese Pharmacopoeia, there may be mentioned dl-α-tocopherol, tocopherol acetate (vitamin E acetate ester), tocopherol succinate (vitamin E succinate ester), etc. As extrapharmacopoeial species, there may be mentioned, for example, α-tocopherol, β-tocopherol, γ-tocopherol, δ-tocopherol, tocopherol nicotinate (vitamin E nicotinate ester), tocopherol phosphate (vitamin E phosphate ester) and tocopherol linolenate (vitamin E linolenate ester).

The term "squalane" as used herein means a saturated hydrocarbon derived by reduction from squalene which is a unsaturated hydrocarbon occurring in the liver oil of deep-sea fish, in particular sharks, or in vegetable oils such as olive oil, rice bran oil, wheat germ oil, sesame oil and cotton seed oil. The term also includes synthetic squalane obtained by synthesis from isoprene.

The above-mentioned vitamin E and squalane both have a curative effect on dermatoses, although the effect is weak, and even when the content of either one is low, a synergistic therapeutic effect can be produced by increasing the content of the other. Even when the contents of both are low, a distinct therapeutic effect can be produced by using the composition continuedly. As for the contents of both in the external preparation, therefore, vitamin E is used preferably in a proportion of 0.1 to 98% by weight, more preferably exceeding 2% by weight to not more than 98% by weight, still more preferably 5 to 60% by weight and most preferably 10 to 50% by weight, while squalane is used in an amount of 2 to 98% by weight, more preferably not less than 2% by weight to less than 98% by weight, still more preferably 5 to 60% by weight and most preferably 10 to 50% by weight.

The external preparation for the treatment of dermatoses according to the first aspect of the present invention may further contain a transdermal absorption enhancer in addition to vitamin E and squalane.

Said transdermal absorption enhancer comprises at least one member selected from the group consisting of N-acylsarcosines (inclusive of salts), higher fatty acid esters, dicarboxylic acids (inclusive of salts), hydroxycarboxylic esters and fatty acid ethanolamides.

As said N-acylsarcosines, there may be mentioned, for example, N-lauroylsarcosine, N-oleoylsarcosine, N-palmitoylsarcosine, cocoacylsarcosine and the like. As the salts thereof, there may be mentioned, for example, the sodium, potassium, magnesium, calcium and aluminum salts of said N-acylsarcosines.

Said higher fatty acid esters are the reaction products of higher fatty acids with alcohols.

Said higher fatty acid contains 10 to 18 carbon atoms; when the number of carbon atoms is smaller, the product higher fatty acid esters are readily volatile and when said number is larger, the transdermal absorption enhancing effect is reduced. Said alcohol should contain 1 to 20 carbon atoms; when the number of carbon atoms is greater, the transdermal absorption enhancing effect is reduced.

As the higher fatty acid having 10 to 18 carbon atoms, there may be mentioned, among others, caprylic acid, lauric acid, myristic acid, palmitic acid, stearic acid and like saturated aliphatic monocarboxylic acids; palmitoleic acid, oleic acid, vaccenic acid, linoleic acid, linolenic acid and like unsaturated aliphatic monocarboxylic acids; and sebacic acid and like saturated aliphataic dicarboxylic acids.

As the alcohol having 1 to 20 carbon atoms, there may be mentioned, among others, aliphatic saturated alcohols such as methyl alcohol, ethyl alcohol, propyl alcohol, isopropyl alcohol, butyl alcohol, isobutyl alcohol, tertiary-butyl alcohol, pentyl alcohol, hexyl alcohol, heptyl alcohol, octyl alcohol, capryl alcohol, nonyl alcohol, decyl alcohol, lauryl alcohol, myristyl alcohol, palmityl alcohol and stearyl alcohol.

As said higher fatty acid esters, there may be mentioned, for example, isopropyl myristate, isopropyl palmitate, isopropyl laurate and isopropyl stearate.

The above-mentioned dicarboxylic acids (inclusive of salts) contain 2 to 10 carbon atoms; when the number of carbon atoms is greater, the transdermal absorption enhancing effect is reduced.

As the dicarboxylic acids having 2 to 10 carbon atoms, there may be mentioned, among others, saturated aliphatic dicarboxylic acids such as oxalic acid, malonic acid, succinic acid, glutaric acid, adipic acid, pimelic acid and suberic acid; unsaturated aliphatic dicarboxylic acids such as fumaric acid and maleic acid; and aromatic dicarboxylic acids such as phthalic acid, isophthalic acid and terephthalic acid. As their salts, there may be mentioned, for example, the sodium, potassium, magnesium, calcium and aluminum salts of the above-mentioned dicarboxylic acids.

Said hydroxycarboxylic esters are the reaction products of hydroxycarboxylic acids with alcohols.

The number of carbon atoms contained in said hydroxycarboxylic acid should be 3 to 6; when smaller, the product hydroxycarboxylic esters are readily volatile and, when greater, the transdermal absorption enhancing effect is reduced. The number of carbon atoms in the alcohol mentioned above should be 1 to 20; when greater, the transdermal absorption enhancing effect is reduced.

As the hydroxycarboxylic acid having 3 to 6 carbon atoms, there may be mentioned, for example, such monocarboxylic acids as lactic acid and glyceric acid and such dicarboxylic acids as malic acid and tartaric acid.

As the alcohol having 1 to 20 carbon atoms, there may be mentioned the same ones as those to be used in the production of the above-mentioned higher fatty acid esters.

As specific examples of the hydroxycarboxylic esters, there may be mentioned, for example, myristyl lactate and cetyl lactate.

Usable as the above-mentioned fatty acid ethanolamides are fatty acid monoethanolamides or fatty acid diethanolamides as well as addition products of these with alkylene oxide.

As said fatty acid ethanolamides, there may be mentioned, for example, lauric acid monoethanolamide, lauric acid diethanolamide, lauroylmonoethanolamide, palmitic acid monoethanolamide, palmitic acid diethanolamide, myristic acid monoethanolamide, myristic acid diethanolamide, lauric acid-myristic acid monoethanolamide, coco fatty acid monoethanolamide, coco fatty acid diethanolamide, polyethoxylated lauroylmonoethanolamide, polyethoxylated coco fatty acid monoethanolamide, etc.

Particularly preferred among the transdermal absorption enhancers mentioned above are N-lauroylsarcosine, isopropyl myristate, isopropyl palmitate, fumaric acid, maleic acid, myristyl lactate, cetyl lactate and lauric acid diethanolamide.

The transdermal absorption enhancer preferably includes, but is not limited to, those mentioned above. Thus, those which are conventional can be used.

As regards the content of said transdermal absorption enhancer in the external preparation, the transdermal absorption enhancer itself can be used also as a base of the preparation in a certain dosage form and thus it is used preferably in a proportion of 0.1 to 10,000 parts by weight, more preferably 0.1 to 100 parts by weight and still more preferably 0.1 to 45 parts by weight, per 100 parts by weight of the sum of vitamin E and squalane.

The dosage form of the external preparation for the treatment of dermatoses according to the first aspect of the present invention is not limited to any particular one but includes, among others, ointments, liniments, lotions and the like prepared by dissolving or dispersing the above-mentioned ingredients in a base material to give the form of cream, paste, jelly, gel, emulsion, solution or the like; cataplasms or poultices and the like prepared by dissolving or dispersing the above-mentioned ingredients in a base material and spreading the mixture on a backing material; plasters, tape-form preparations and the like prepared by dissolving or dispersing the above-mentioned ingredients in an adhesive material and spreading the mixture on a backing material; and so forth. It is also possible to prepare liniments by using vitamin E and squalane alone without using any base material.

Said base material may be any of those pharmaceutically acceptable base materials which are known for use in preparing ointments, liniments, lotions and the like. Thus, it includes, among others, polymers such as sodium alginate, gelatin, corn starch, gum tragacanth, methylcellulose, hydroxyethylcellulose, carboxymethylcellulose, xanthan gum, dextrin, carboxymethylstarch, polyvinyl alcohol, sodium polyacrylate, methoxyethylene-maleic anhydride copolymer, polyvinyl ether, polyvinylpyrrolidone, etc.; fats and oils such as beeswax, olive oil, cacao butter, sesame oil, soybean oil, camellia oil, peanut oil, beef fat, lard, lanolin, etc.; white petrolatum; paraffins; hydrocarbon gel ointments (e.g. Plastibase, trademark, available from Taisho Pharmaceutical Co.); higher fatty acids such as stearic acid; higher alcohols such as cetyl alcohol, stearyl alcohol, etc.; polyethylene glycol; and water.

Furthermore, inorganic fillers such as kaolin, bentonite, zinc oxide, titanium oxide, etc., viscosity modifiers, antioxidants, pH adjusting agents, humectants such as glycerol, propylene glycol, etc. and other additives may be incorporated as necessary.

Said backing material may suitably be selected depending on the dosage form selected (e.g. capaplasm, plaster, tape-form preparation) but is preferably impermeable or hardly permeable to the active ingredients and soft and flexible. Thus, it includes, among others, resin films such as cellulose acetate, ethylcellulose, polyethylene, polypropylene, polyvinyl chloride, vinyl acetate-vinyl chloride copolymers, ethylene-vinyl acetate copolymers, ethylene-vinyl acetate-carbon monoxide copolymers, ethylene-butyl acrylate-carbon monoxide copolymers, polyvinylidene chloride, polyurethanes, nylons, polyethylene terephthalate, polybutylene terephthalate, etc., aluminum sheet, woven fabrics, nonwoven fabrics and the like, and laminated sheets derived from these.

Said adhesive material may be any of those known adhesive materials which are pharmaceutically acceptable. Thus, for example, acrylic adhesives, rubber-based adhesives, silicone adhesives, urethane type adhesives and the like may be mentioned and, among them, acrylic adhesives and rubber-based adhesives are preferred. In the case of spreading onto the backing material mentioned above, the adhesive material may be of the solvent, emulsion or hot-melt type or of any other appropriate type.

As the acrylic adhesives mentioned above, there may be mentioned polyalkyl (meth)acrylate-based adhesives prepared by copolymerizing alkyl (meth)acrylates as well as copolymers of an alkyl (meth)acrylate(s) and a polyfunctional monomer(s) copolymerizable therewith and/or some other vinyl monomer or monomers.

As said alkyl (meth)acrylates, there may be mentioned, for example, 2-ethylhexyl (meth)acrylate, dodecyl (meth) acrylate and the like.

As said polyfunctional monomers, there may be mentioned, for example, 1,6-hexylene glycol dimethacrylate, tetraethylene glycol diacrylate and the like. As said other vinyl monomers, there may be mentioned, for example, N-vinyl-2-pyrrolidone, vinyl acetate and the like.

As said rubber-based adhesives, there may be mentioned adhesive compositions mainly comprising natural rubber, styrene-isoprene-styrene block copolymers, styrene-olefin-styrene block copolymers and the like. They generally contain tackifiers such as rosin, hydrogenated rosin, rosin esters, terpene resins, terpene-phenol resins, petroleum resins, coumaron resins, coumaron-indene resins, etc. as added thereto.

The dose of the external preparation for the treatment of dermatoses according to the first aspect of the present invention may vary depending on the disease to be treated, the severity of symptoms, the size of the affected part and other factors but is preferably 0.01 to 10 grams daily. Such daily dose is applied to the affected part once or in several appropriate divided doses.

As the target diseases to be treated with the external preparation for the treatment of dermatoses according to the first aspect of the present invention, there may be mentioned, for example, rough dry skin, rash, miliaria, sore, chilblains, diaper rash, atopic dermatitis, contact dermatitis, seborrheic dermatitis, lichen Vidal, nummular eczema, housewives' eczema, solar dermatitis, insect bites, pruritus cutaneous, prurigo, drug eruption, toxicoderma, psoriasis, parapsoriasis, pustulosis palmaris et plantaris, lichen planus, lichen nitidus, pityriasis rubra pilaris, pityriasis rosea Gibert, erythema, erythroderma, discoid lupus erythematosus, systemic lupus erythematosus, pemphigus, pemphigoid, Duhring's dermatitis herpetiformis, alopecia areata, vitiligo vulgaris, sarcoidosis, amyloidosis cutis, keloid, hypertrophic scar, wound, bedsore, skin ulcer, alopecia, hair growing and hair restoration.

The second aspect of the present invention is now described in further detail.

The external preparation for the treatment of dermatoses according to the second aspect of the present invention comprises an adrenocortical hormone, vitamin E and squalane.

Said adrenocortical hormone includes hormones secreted from the adrenal cortex and derivatives thereof, such as alclometasone dipropionate, triamcinolone acetonide, fluocinolone acetonide, amcinonide, clobetasol propionate, clobetasone butyrate, cortisone acetate, diflorasone diacetate, diflucortolone valerate, diflucortolone acetate, difluprednate, dexamethasone, dexamethasone palmitate, dexamethasone propionate, dexamethasone sodium m-sulfobenzoate, dexamethasone sodium phosphate, dexamethasone valerate, dexamethasone acetate, dexamethasone sodium sulfate, triamcinolone acetate, paramethasone, paramethasone acetate, halcinonide, halopredone acetate, hydrocortisone, hydrocortisone sodium succinate, hydrocortisone sodium phosphate, hydrocortisone acetate, hydrocortisone acetate propionate, hydrocortisone butyrate, budesonide, prasterone, fluocinonide, fluorometholone, fluorocortisone acetate, fluoroxycortide, flumethasone, flumethasone pivalate, prednisolone, prednisolone succinate, methylprednisolone succinate, prednisolone butylacetate, methylprednisolone, methylprednisolone sodium succinate, prednisolone sodium phosphate, prednisolone valerate, prednisolone valerate acetate, prednisolone acetate, methylprednisolone acetate, prednisone, beclometasone, beclometasone propionate, betamethasone, betamethasone dipropionate, betamethasone sodium phosphate, betamethasone valerate, betamethasone acetate, etc.

The content of the adrenocortical hormone in the external preparation is preferably 0.0001 to 2% by weight, more preferably 0.001 to 1% by weight; at lower content levels, the curative effect on dermatoses will be unsatisfactory, while, at higher levels, side effects will readily be produced although an increased curative effect may be obtained.

The above-mentioned vitamin E includes those species mentioned in relation to the first aspect of the present invention.

The vitamin E content in the external preparation is preferably 0.1 to 99% by weight, more preferably 0.2 to 80% by weight and still more preferably 0.5 to 50% by weight; when said content is lower, the therapeutic effect on dermatoses will be unsatisfactory, while, at higher content levels, the therapeutic effect will no more increase with the content and, with certain base materials, it becomes difficult to maintain the dosage form.

The above-mentioned squalane includes those species mentioned in relation to the first aspect of the present invention.

The squalane content in the external preparation is preferably 0.1 to 99% by weight, more preferably 1 to 80% by weight and still more preferably 5 to 50%; when said content is lower, the therapeutic effect on dermatoses will be unsatisfactory while, at higher content levels, the therapeutic effect will no more increase with the content and, with certain base materials, it becomes difficult to maintain the dosage form.

A particularly preferred combination of the contents of the respective active ingredients in the external preparation is as follows: 0.001 to 0.5% by weight of adrenocortical hormone, 0.5 to 20% by weight of vitamin E and 10 to 30% by weight of squalane.

The external preparation for the treatment of dermatoses according to the second aspect of the present invention may further contain at least one transdermal absorption enhancer selected from the group consisting of N-acylsarcosines (inclusive of salts), higher fatty acid esters which are reaction products from a higher fatty acid having 10 to 18 carbon atoms and an alcohol having 1 to 20 carbon atoms, dicarboxylic acids having 2 to 10 carbon atoms (inclusive of salts), hydroxycarboxylic esters which are reaction products from a hydroxycarboxylic acid having 3 to 6 carbon atoms and an alcohol having 1 to 20 carbon atoms, and fatty acid ethanolamides.

Said N-acylsarcosines (inclusive of salts) include, among others, those species mentioned hereinabove in relation to the first aspect of the present invention.

Said higher fatty acid esters are reaction products derived from a higher fatty acid and an alcohol. The number of carbon atoms contained in said higher fatty acid should be 10 to 18; when said number is smaller, the reaction products, higher fatty acid esters will be readily volatile, whereas the transdermal absorption enhancing effect will be low when said number is larger. The number of carbon atoms contained in said alcohol should be 1 to 20; when said number is larger, the transdermal absorption enhancing effect will be low.

The higher fatty acid having 10 to 18 carbon atoms includes, among others, those species mentioned above in relation to the first aspect of the present invention.

The alcohol having 1 to 20 carbon atoms includes, among others, those species mentioned above in relation to the first aspect of the present invention.

Said higher fatty acid esters include, among others, those species mentioned above in relation to the first aspect of the present invention.

The number of carbon atoms contained in said dicarboxylic acids (inclusive of salts) should be 2 to 10; when said number is greater, the transdermal absorption enhancing effect will be low.

As examples of the dicarboxylic acids having 2 to 10 carbon atoms (inclusive of salts), there may be mentioned those species mentioned above in relation to the first aspect of the present invention.

The number of carbon atoms contained in said hydroxycarboxylic acid should be 3 to 6; when said number is smaller, the product hydroxycarboxylic esters will be readily volatile and when it is greater, the transdermal absorption enhancing effect will be low. The number of carbon atoms contained in said alcohol should be 1 to 20 since, when it is greater, the transdermal absorption enhancing effect will be low.

As examples of the hydroxycarboxylic acid having 3 to 6 carbon atoms, there may be mentioned those species mentioned above in relation to the first aspect of the present invention.

The alcohol having 1 to 20 carbon atoms includes those species to be used in the reaction for producing the above-mentioned higher fatty acid esters.

As examples of said hydroxycarboxylic acid esters, there may be mentioned those species mentioned above in relation to the first aspect of the present invention.

Said fatty acid ethanolamides include fatty acid monoethanolamides and fatty acid diethanolamides as well as addition products derived therefrom with alkylene oxide.

As examples of such fatty acid ethanolamides, there may be mentioned those species mentioned above in relation to the first aspect of the present invention.

Particularly preferred among the above-mentioned transdermal absorption enhancers are N-lauroylsarcosine, isopropyl myristate, isopropyl palmitate, fumaric acid, maleic acid, myristyl lactate, cetyl lactate and lauric acid diethanolamide.

While those enhancers mentioned above are preferred, any other known transdermal absorption enhancer can also be used.

The content of the above transdermal absorption enhancer in the external preparation for the treatment of dermatoses is preferably 0.1 to 25 parts by weight, more preferably 1 to 12 parts by weight, per 100 parts by weight of the sum total of the adrenocortical hormone, vitamin E and squalane; when said content is lower, the transdermal absorption enhancing effect will be produced only to an unsatisfactory extent whereas when said content is higher, a skin irritating effect may be produced or the fluidity will be too high, so that, with certain bases, it will be difficult for the dosage form to hold its shape.

The dosage form of the external preparation for the treatment of dermatoses according to the second aspect of the present invention is not limited to any particular one but includes, among others, those mentioned above in relation to the first aspect of the present invention. When the composition is prepared from an adrenocortical hormone, vitamin E and squalane alone without using any base, there is obtained a liniment.

The base may be any of those which are pharmaceutically acceptable. Thus, those which are known as bases for ointments, liniments, lotions and the like can be used. As examples, there may be mentioned those mentioned above in relation to the first aspect of the present invention.

Furthermore, where necessary, inorganic fillers such as kaolin, bentonite, zinc oxide, titanium oxide, etc.; viscosity modifiers; antioxidants; pH adjusting agents; and humectants such as glycerol, propylene glycol, etc. may be added.

The backing material can suitably be selected according to the dosage form (e.g. cataplasm, plaster, tape-form preparation, etc.) but is preferably one flexible and impermeable or scarcely permeable to the active ingredients. Examples are those mentioned above in relation to the first aspect of the present invention.

The adhesive material may be any of those materials which are known to be pharmaceutically acceptable. Examples are those mentioned above in relation to the first aspect of the present invention. When the composition is to be spread on a support, the adhesive material may be of the solvent, emulsion or hot melt type, for instance.

The dose of the external preparation for the treatment of dermatoses according to the second aspect of the present invention may vary depending on the disease to be treated, the severity of symptoms, the size of the affected part and other factors but preferably is 0.01 to 10 g daily. Such daily dose is applied to the affected part all at once or in appropriately divided doses.

The diseases to be treated with the external preparation for the treatment of dermatoses according to the second aspect of the present invention include, among others, those mentioned above in relation to the first aspect of the present invention.

Now, the third aspect of the present invention is described in further detail.

The external preparation for the treatment of dermatoses according to the third aspect of the present invention comprises a nonsteroidal antiinflammatory agent, vitamin E and squalane and/or squalene.

Said nonsteroidal antiinflammatory agent includes those ones which are used in known external preparations for dermatoses, such as bufexamac, bendazac, suprofen, ufenamate, ibuprofen piconol, crotamiton, glycyrrhetic acid, etc. Other nonsteroidal antiinflammatory agents such as aspirin, indomethacin, diclofenac and ibuprofen may also be used.

The content of the nonsteroidal antiinflammatory agent in the external preparation is preferably 0.5 to 20% by weight; when said content is lower, the curative effect on dermatoses will be unsatisfactory whereas a higher content tends to produce side effects, althouth the curative effect will be high. Preferred contents of individual nonsteroidal antiinflammatory agents are, for example, as follows: bufexamac—about 5% by weight; bendazac—about 3% by weight; suprofen—about 1% by weight; ufenamate—about 5% by weight; ibuprofen piconol—about 5% by weight; crotamiton—about 10% by weight; and glycyrrhetic acid—about 2% by weight.

As species of said vitamin E, there may be mentioned, among others, those mentioned above in relation to the first aspect of the present invention.

The content of vitamin E in the external preparation is preferably 0.1 to 99% by weight, more preferably 0.2 to 80% by weight and still more preferably 0.5 to 50% by weight; when said content is smaller, the curative effect on dermatoses will be weak, while a higher content may make it difficult for the dosage form to hold its shape with certain base materials.

The term "squalene" as used herein means an unsaturated hydrocarbon occurring in the liver oil of deep-sea fish, in particular sharks, or in vegetable oils such as olive oil, rice bran oil, wheat germ oil, sesame oil, cotton seed oil, etc., and even in human serum cutaneum. Squalane is a saturated hydrocarbon derived from said squalene by reduction. It also includes synthetic squalane obtained by synthesis from isoprene.

The content of squalane and/or squalene in the external preparation is preferably 0.1 to 99% by weight, more preferably 0.1 to 80% by weight and still more preferably 0.5 to 60% by weight; when said content is smaller, the curative effect on dermatoses will be weak while a higher content may make it difficult for the dosage form to hold its shape with certain base materials.

A particularly preferred combination of the contents of respective active ingredients in the external preparation is as follows: nonsteroidal antiinflammatory agent—0.5 to 20% by weight; vitamin E—0.5 to 50% by weight; and squalane and/or squalene—10 to 50%.

Said vitamin E as well as squalane and/or squalene each individually has a curative effect on dermatoses, although said effect is weak and, even when the content of either is low, a synergistic therapeutic effect can be produced in cooperation with the nonsteroidal antiinflammatory agent by increasing the content of the other.

The external preparation for the treatment of dermatoses according to the third aspect of the present invention may further contain at least one transdermal absorption enhancer selected from the group consisting of N-acylsarcosines (inclusive of salts), higher fatty acid esters which are products from a higher fatty acid having 10 to 18 carbon atoms and an alcohol having 1 to 20 carbon atoms, dicarboxylic acids having 2 to 10 carbon atoms (inclusive of salts), hydroxycarboxylic acid esters which are reaction products from a hydroxycarboxylic acid having 3 to 6 carbon atoms and an alcohol having 1 to 20 carbon atoms, and fatty acid ethanolamides.

Said N-acylsarcosines (inclusive of salts) include, among others, those species mentioned hereinabove in relation to the first aspect of the present invention.

Said higher fatty acid esters are reaction products from a higher fatty acid and an alcohol. The number of carbon atoms contained in said higher fatty acid should be 10 to 18; when said number is smaller, the higher fatty acid esters will be readily volatile whereas the transdermal absorption enhancing effect will be low when said number is larger. The number of carbon atoms contained in said alcohol should be 1 to 20; when said number is larger, the transdermal absorption enhancing effect will be low.

The higher fatty acid having 10 to 18 carbon atoms includes, among others, those species mentioned above in relation to the first aspect of the present invention.

The alcohol having 1 to 20 carbon atoms includes, among others, those species mentioned above in relation to the first aspect of the present invention.

Said higher fatty acid esters include, among others, those species mentioned above in relation to the first aspect of the present invention.

The number of carbon atoms contained in said dicarboxylic acids (inclusive of salts) should be 2 to 10; when said number is greater, the transdermal absorption enhancing effect will be low.

As examples of the dicarboxylic acids having 2 to 10 carbon atoms (inclusive of salts), there may be mentioned those species mentioned above in relation to the first aspect of the present invention.

Said hydroxycarboxylic acid esters are reaction products from a hydroxycarboxylic acid and an alcohol.

The number of carbon atoms contained in said hydroxycarboxylic acid should be 3 to 6; when said number is smaller, the product hydroxycarboxylic acid esters will be readily volatile and when it is greater, the transdermal absorption enhancing effect will be low. The number of carbon atoms contained in said alcohol should be 1 to 20 since, when it is greater, the transdermal absorption enhancing effect will be low.

As examples of the hydroxycarboxylic acid having 3 to 6 carbon atoms, there may be mentioned those species mentioned above in relation to the first aspect of the present invention.

The alcohol having 1 to 20 carbon atoms includes those species to be used in the reaction for producing the above-mentioned higher fatty acid esters.

As examples of said hydroxycarboxylic acid esters, there may be mentioned those species mentioned above in relation to the first aspect of the present invention.

Said fatty acid ethanolamides include fatty acid monoethanolamides and fatty acid diethanolamides as well as addition products derived therefrom with alkylene oxide.

As examples of such fatty acid ethanolamides, there may be mentioned those species mentioned above in relation to the first aspect of the present invention.

Particularly preferred among the above-mentioned transdermal absorption enhancers are N-lauroylsarcosine, isopropyl myristate, isopropyl palmitate, fumaric acid, maleic acid, myristyl lactate, cetyl lactate and lauric acid diethanolamide.

While those enhancers mentioned above are preferred, any other known transdermal absorption enhancer can also be used.

The content of the above transdermal absorption enhancer in the external preparation is preferably 0.01 to 250 parts by weight, more preferably 0.5 to 100 parts by weight, per 100 parts by weight of the sum total of the nonsteroidal antiinflammatory agent, vitamin E and squalane and/or squalene; when said content is lower, the transdermal absorption enhancing effect will be produced only to an unsatisfactory extent whereas when said content is higher, a skin irritating effect may be produced or the fluidity will be too high, so that, with certain bases, it will be difficult for the dosage form to hold its shape.

The dosage form of the external preparation for the treatment of dermatoses according to the third aspect of the present invention is not limited to any particular one but includes, among others, those mentioned above in relation to the first aspect of the present invention.

The base may be any of those which are pharmaceutically acceptable. Thus, those which are known as bases for ointments, liniments, lotions and the like can be used. As examples, there may be mentioned those mentioned above in relation to the first aspect of the present invention.

Furthermore, where necessary, such additives as inorganic fillers (e.g. kaolin, bentonite, zinc oxide, titanium oxide, etc.); viscosity modifiers; antioxidants; pH adjusting agents; and humectants such as glycerol, propylene glycol, etc. may be added.

The backing material can suitably be selected according to the dosage form (e.g. cataplasm, plaster, tape-form preparation, etc.) but is preferably one flexible and impermeable or scarcely permeable to the active ingredients. Examples are those mentioned above in relation to the first aspect of the present invention.

The adhesive material may be any of those materials which are known to be pharmaceutically acceptable. Examples are those mentioned above in relation to the first aspect of the present invention. When the composition is to be spread on a support, the adhesive material may be of the solvent, emulsion or hot melt type, for instance.

The dose of the external preparation for the treatment of dermatoses according to the third aspect of the present invention may vary depending on the disease to be treated, the severity of symptoms, the size of the affected part and other factors but preferably is 0.01 to 10 g daily. Such daily dose is applied to the affected part all at once or in appropriately divided doses.

The diseases to be treated with the external preparation for the treatment of dermatoses according to the third aspect of the present invention include, among others, those mentioned above in relation to the first aspect of the present invention.

Now, the fourth aspect of the present invention is described in further detail.

The external preparation for the treatment of dermatoses according to the fourth aspect of the present invention comprises an antihistaminic agent, vitamin E and squalane and/or squalene.

Said antihistaminic agent includes, among others, those commonly used in external preparations for dermatoses, for example isothipendyl hydrochloride, diphenhydramine, diphenhydramine lauryl sulfate, etc.

The content of the antihistaminic agent in the external preparation is preferably 0.1 to 10% by weight; when said content is lower, the therapeutic effect on dermatoses will be unsatisfactory whereas a higher content tends to produce side effects, although the therapeutic effect is higher. Preferred contents of individual antihistaminic agents are, for example, as follows: isothipendyl hydrochloride—about 0.75% by weight; diphenhydramine—about 1% by weight; and diphenhydramine lauryl sulfate—about 4% by weight.

As species of said vitamin E, there may be mentioned, among others, those mentioned above in relation to the first aspect of the present invention.

The content of vitamin E in the external preparation is preferably 0.1 to 99% by weight, more preferably 0.2 to 80% by weight and still more preferably 0.5 to 50% by weight; when said content is smaller, the curative effect on dermatoses will be weak while a higher content may make it difficult for the dosage form to hold its shape with certain base materials.

Said squalane and/or squalene includes, among others, those species mentioned above in relation to the third aspect of the present invention.

The content of squalane and/or squalene in the external preparation is preferably 0.1 to 99% by weight, more preferably 0.1 to 80% by weight and still more preferably 0.5 to 60% by weight; when said content is smaller, the curative effect on dermatoses will be weak while a higher content may make it difficult for the dosage form to hold its shape with certain base materials.

A particularly preferred combination of the contents of respective active ingredients in the external preparation is as follows: antihistaminic agent—0.1 to 10% by weight; vitamin E—0.5 to 50% by weight; and squalane and/or squalene—10 to 50% by weight.

Said vitamin E as well as squalane and/or squalene each individually has a curative effect on dermatoses, although said effect is weak and, even when the content of either is low, a synergistic therapeutic effect can be produced in cooperation with the antihistaminic agent by increasing the content of the other.

The external preparation for the treatment of dermatoses according to the fourth aspect of the present invention may further contain at least one transdermal absorption enhancer selected from the group consisting of N-acylsarcosines (inclusive of salts), higher fatty acid esters which are reaction products from a higher fatty acid having 10 to 18 carbon atoms and an alcohol having 1 to 20 carbon atoms, dicarboxylic acids having 2 to 10 carbon atoms (inclusive of salts), hydroxycarboxylic acid esters which are reaction products from a hydroxycarboxylic acid having 3 to 6 carbon atoms and an alcohol having 1 to 20 carbon atoms, and fatty acid ethanolamides.

Said N-acylsarcosines (inclusive of salts) include, among others, those species mentioned hereinabove in relation to the first aspect of the present invention.

Said higher fatty acid esters are reaction products from a higher fatty acid and an alcohol. The number of carbon atoms contained in said higher fatty acid should be 10 to 18; when said number is smaller, the higher fatty acid esters will be readily volatile whereas the transdermal absorption enhancing effect will be low when said number is larger. The number of carbon atoms contained in said alcohol should be 1 to 20; when said number is larger, the transdermal absorption enhancing effect will be low.

The higher fatty acid having 10 to 18 carbon atoms includes, among others, those species mentioned above in relation to the first aspect of the present invention.

The alcohol having 1 to 20 carbon atoms includes, among others, those species mentioned above in relation to the first aspect of the present invention.

Said higher fatty acid esters include, among others, those species mentioned above in relation to the first aspect of the present invention.

The number of carbon atoms contained in said dicarboxylic acids (inclusive of salts) should be 2 to 10; when said number is greater, the transdermal absorption enhancing effect will be low.

As examples of the dicarboxylic acids having 2 to 10 carbon atoms (inclusive of salts), there may be mentioned those species mentioned above in relation to the first aspect of the present invention.

Said hydroxycarboxylic acid esters are reaction products from a hydroxycarboxylic acid and an alcohol.

The number of carbon atoms contained in said hydroxycarboxylic acid should be 3 to 6; when said number is smaller, the product hydroxycarboxylic acid esters will be readily volatile and when it is greater, the transdermal absorption enhancing effect will be low. The number of carbon atoms contained in said alcohol should be 1 to 20 since, when it is greater, the transdermal absorption enhancing effect will be low.

As examples of the hydroxycarboxylic acid having 3 to 6 carbon atoms, there may be mentioned those species mentioned above in relation to the first aspect of the present invention.

The alcohol having 1 to 20 carbon atoms includes those species to be used in the reaction for producing the above-mentioned higher fatty acid esters.

As examples of said hydroxycarboxylic acid esters, there may be mentioned those species mentioned above in relation to the first aspect of the present invention.

Said fatty acid ethanolamides include fatty acid monoethanolamides and fatty acid diethanolamides as well as addition products derived therefrom with alkylene oxide.

As examples of such fatty acid ethanolamides, there may be mentioned those species mentioned above in relation to the first aspect of the present invention.

Particularly preferred among the above-mentioned transdermal absorption enhancers are N-lauroylsarcosine, isopropyl myristate, isopropyl palmitate, fumaric acid, maleic acid, myristyl lactate, cetyl lactate and lauric acid diethanolamide.

While those enhancers mentioned above are preferred, any other known transdermal absorption enhancer can also be used.

The content of the above transdermal absorption enhancer in the external preparation is preferably 0.01 to 250 parts by weight, more preferably 0.5 to 100 parts by weight, per 100 parts by weight of the sum total of the antihistaminic agent, vitamin E and squalane and/or squalene; when said content is lower, the transdermal absorption enhancing effect will be produced only to an unsatisfactory extent whereas when said content is higher, a skin irritating effect may be produced or the fluidity will be too high, so that, with certain bases, it will be difficult for the dosage form to hold its shape.

The dosage form of the external preparation for the treatment of dermatoses according to the fourth aspect of the present invention is not limited to any particular one but includes, among others, those mentioned above in relation to the first aspect of the present invention.

The base may be any of those which are pharmaceutically acceptable. Thus, those which are known as bases for ointments, liniments, lotions and the like can be used. As examples, there may be mentioned those mentioned above in relation to the first aspect of the present invention.

Furthermore, where necessary, such additives as inorganic fillers (e.g. kaolin, bentonite, zinc oxide, titanium oxide, etc.); viscosity modifiers; antioxidants; pH adjusting agents; and humectants such as glycerol, propylene glycol, etc. may be added.

The backing material can suitably be selected according to the dosage form (e.g. cataplasm, plaster, tape-form preparation, etc.) but is preferably one flexible and impermeable or scarcely permeable to the active ingredients. Examples are those mentioned above in relation to the first aspect of the present invention.

The adhesive material may be any of those materials which are known to be pharmaceutically acceptable. Examples are those mentioned above in relation to the first aspect of the present invention. When the composition is to be spread on a support, the adhesive material may be of the solvent, emulsion or hot melt type, for instance.

The dose of the external preparation for the treatment of dermatoses according to the fourth aspect of the present invention may vary depending on the disease to be treated, the severity of symptoms, the size of the affected part and other factors but preferably is 0.01 to 10 g daily. Such daily dose is applied to the affected part all at once or in appropriately divided doses.

The diseases to be treated with the external preparation for the treatment of dermatoses according to the fourth aspect of the present invention include, among others, those mentioned above in relation to the first aspect of the present invention.

Now, the fifth aspect of the present invention is described in further detail.

The external preparation for the treatment of dermatoses according to the fifth aspect of the present invention comprises vitamin E, squalene and squalane.

As species of said vitamin E, there may be mentioned, among others, those mentioned above in relation to the first aspect of the present invention.

The content of vitamin E in the external preparation is preferably 0.1 to 99.8% by weight, more preferably 2 to 80% by weight and still more preferably 5 to 60% by weight; when said content is smaller, the curative effect on dermatoses will be unsatisfactory while, at higher contents, the therapeutic effect will no more increase with the increase in content and, with certain bases, it will be difficult for the dosage form to hold its shape.

Said squalene and/or squalane includes, among others, those species mentioned above in relation to the third aspect of the present invention.

The content of squalene in the external preparation is preferably 0.1 to 99.8% by weight, more preferably 0.1 to 80% by weight and still more preferably 0.5 to 40% by weight; when said content is smaller, the curative effect on dermatoses will be weak whereas, at higher contents, the therapeutic effect will no more increase with the increase in content and, with certain bases, it will be difficult for the dosage form to hold its shape.

The content of squalane in the external preparation is preferably 0.1 to 99.8% by weight, more preferably 0.1 to 80% by weight and still more preferably 0.5 to 60% by weight; when said content is smaller, the curative effect on dermatoses will be weak whereas, at higher contents, the therapeutic effect will no more increase with the increase in content and, with certain bases, it will be difficult for the dosage form to hold its shape.

A particularly preferred combination of the contents of respective active ingredients in the external preparation is as follows: vitamin E—10 to 50% by weight; squalene—1.5 to 30% by weight; and squalane—2 to 45% by weight.

The external preparation for the treatment of dermatoses according to the fifth aspect of the present invention may further contain at least one transdermal absorption enhancer selected from the group consisting of N-acylsarcosines (inclusive of salts), higher fatty acid esters which are reaction products from a higher fatty acid having 10 to 18 carbon atoms and an alcohol having 1 to 20 carbon atoms, dicarboxylic acids having 2 to 10 carbon atoms (inclusive of salts), hydroxycarboxylic acid esters which are reaction products from a hydroxycarboxylic acid having 3 to 6 carbon atoms and an alcohol having 1 to 20 carbon atoms, and fatty acid ethanolamides.

Said N-acylsarcosines (inclusive of salts) include, among others, those species mentioned hereinabove in relation to the first aspect of the present invention.

Said higher fatty acid esters are reaction products from a higher fatty acid and an alcohol. The number of carbon atoms contained in said higher fatty acid should be 10 to 18; when said number is smaller, the reaction products, higher fatty acid esters will be readily volatile whereas the transdermal absorption enhancing effect will be low when said number is larger. The number of carbon atoms contained in said alcohol should be 1 to 20; when said number is larger, the transdermal absorption enhancing effect will be low.

The higher fatty acid having 10 to 18 carbon atoms includes, among others, those species mentioned above in relation to the first aspect of the present invention.

The alcohol having 1 to 20 carbon atoms includes, among others, those species mentioned above in relation to the first aspect of the present invention.

Said higher fatty acid esters include, among others, those species mentioned above in relation to the first aspect of the present invention.

The number of carbon atoms contained in said dicarboxylic acids (inclusive of salts) should be 2 to 10; when said number is greater, the transdermal absorption enhancing effect will be low.

As examples of the dicarboxylic acids having 2 to 10 carbon atoms (inclusive of salts), there may be mentioned those species mentioned above in relation to the first aspect of the present invention.

Said hydroxycarboxylic acid esters are reaction products from a hydroxycarboxylic acid and an alcohol.

The number of carbon atoms contained in said hydroxycarboxylic acid should be 3 to 6; when said number is smaller, the product hydroxycarboxylic acid esters will be readily volatile and when it is greater, the transdermal absorption enhancing effect will be low. The number of carbon atoms contained in said alcohol should be 1 to 20 since, when it is greater, the transdermal absorption enhancing effect will be low.

As examples of the hydroxycarboxylic acid having 3 to 6 carbon atoms, there may be mentioned those species mentioned above in relation to the first aspect of the present invention.

The alcohol having 1 to 20 carbon atoms includes those species to be used in the reaction for producing the above-mentioned higher fatty acid esters.

As examples of said hydroxycarboxylic acid esters, there may be mentioned those species mentioned above in relation to the first aspect of the present invention.

Said fatty acid ethanolamides include fatty acid monoethanolamides and fatty acid diethanolamides as well as addition products derived therefrom with alkylene oxide.

As examples of such fatty acid ethanolamides, there may be mentioned those species mentioned above in relation to the first aspect of the present invention.

Particularly preferred among the above-mentioned transdermal absorption enhancers are N-lauroylsarcosine, isopropyl myristate, isopropyl palmitate, fumaric acid, maleic acid, myristyl lactate, cetyl lactate and lauric acid diethanolamide.

While those enhancers mentioned above are preferred, any other known transdermal absorption enhancer can also be used.

The content of the above transdermal absorption enhancer in the external preparation is preferably 0.01 to 250 parts by weight, more preferably 0.5 to 100 parts by weight, per 100 parts by weight of the sum total of vitamin E, squalene and squalane; when said content is lower, the transdermal absorption enhancing effect will be produced only to an unsatisfactory extent whereas when said content is higher, a skin irritating effect may be produced or the fluidity will be too high, so that, with certain bases, it will be difficult for the dosage form to hold its shape.

The dosage form of the external preparation for the treatment of dermatoses according to the fifth aspect of the present invention is not limited to any particular one but includes, among others, those mentioned above in relation to the first aspect of the present invention.

The base may be any of those which are pharmaceutically acceptable. Thus, those which are known as bases for ointments, liniments, lotions and the like can be used. As examples, there may be mentioned those mentioned above in relation to the first aspect of the present invention.

Furthermore, where necessary, such additives as inorganic fillers (e.g. kaolin, bentonite, zinc oxide, titanium oxide, etc.); viscosity modifiers; antioxidants; pH adjusting agents; and humectants such as glycerol, propylene glycol, etc. may be added.

The backing material can suitably be selected according to the dosage form (e.g. cataplasm, plaster, tape-form preparation, etc.) but is preferably one flexible and impermeable or scarcely permeable to the active ingredients. Examples are those mentioned above in relation to the first aspect of the present invention.

The adhesive material may be any of those materials which are known to be pharmaceutically acceptable. Examples are those mentioned above in relation to the first aspect of the present invention. When the composition is to be spread on a support, the adhesive material may be of the solvent, emulsion or hot melt type, for instance.

The dose of the external preparation for the treatment of dermatoses according to the fifth aspect of the present invention may vary depending on the disease to be treated, the severity of symptoms, the size of the affected part and other factors but preferably is 0.01 to 10 g daily. Such daily dose is applied to the affected part all at once or in appropriately divided doses.

The diseases to be treated with the external preparation for the treatment of dermatoses according to the fifth aspect of the present invention include, among others, those mentioned above in relation to the first aspect of the present invention.

BEST MODES FOR CARRYING OUT THE INVENTION

The following examples are further illustrative of the present invention but are by no means limitative of the scope thereof.

EXAMPLES 1 TO 24 AND COMPARATIVE EXAMPLES 1 TO 10

Ointments were prepared by supplying Plastibase (Taisho Pharmaceutical), vitamin E acetate (Wako Pure Chemical Industries), vitamin E nicotinate (Wako Pure Chemical Industries), vitamin E succinate (Sigma Chemical), squalane (Wako Pure Chemical Industries), isopropyl myristate (Nacalai Tesque), dexamethasone (Wako Pure Chemical Industries) and prednisolone (Wako Pure Chemical Industries), in amounts specified below in Tables 1 to 3, to a mortar, and kneading the mortar contents until the components other than Plastibase were dissolved in the latter. In Examples 13, 14, 16 and 17, Plastibase was not used, hence the preparations prepared were liniments.

The thus-obtained ointments and liniments were subjected to tests 1 to 5 described below (except for the ointment obtained in Example 18, which was not tested). In each test run, five rats were used and the results were expressed in terms of mean value.

TEST EXAMPLE 1

Effect on DNCB-induced Primary Skin Irritation (nonallergic dermal inflammatory reaction)

After the frank of 7-week-old Wistar rats was clipped of hairs, 20 µl of 2% 2,4-dinitrochlorobenzene (DNCB, Wako Pure Chemical Industries)-acetone was applied to the exposed skin area and let dry thoroughly to induce nonallergic dermatitis.

Then, 0.1 g samples from the ointments or liniments obtained in the foregoing examples and comparative examples were respectively deposited on a 1 cm (radius) disk of polyethylene sheet and applied against the site of DNCB-induced dermatitis.

Twenty-four hours after induction of dermatitis, the intensity of local erythema was evaluated using a chromameter (CR-200, Minolta).

In a control run, the ointment base (Plastibase) alone was applied in lieu of the test preparation and erythema intensity measurement was performed in the same manner.

From the results of measurement of the erythema intensity (A) at the site of application of the control and the erythema intensity (B) at the site of application of the test preparation, the erythema inhibition percentage was calculated as follows:

Erythema inhibition (%)=[(A−B)/A]×100

The results thus obtained are shown in Tables 1 to 3.

TEST EXAMPLE 2

Effect on PCA reaction (type I allergic reaction)
(1) Preparation of Rat Anti-DNP-As Serum Rat anti-DNP-As serum was prepared by the method of Tada and Okumura (Journal of Immunology; 106, 1002, 1971).

Thus, an *Ascaris suum* (swine roundworm) extract was prepared by the method of Strejan and Campbell (Journal of Immunology; 98, 893, 1967), and then treated with 2,4-dinitrofenyl sulfate (DNP) by the method of Eisen et al. (Journal of American Chemical Society; 75, 4583, 1953) to give DNP-bound *Ascaris suum* (DNP-As).

The above DNP-As (1 mg) was dissolved in 1 ml of physiological saline containing 1×1010 killed cells of *Bordetella pertussis* as suspended therein and the resulting suspension was administered to female rats weighing about 200 mg by subcutaneous injection into the dorsum of each foot. After 5 days, 0.5 mg of DNP-As was dissolved in 0.5 ml of physiological saline and the solution was injected into the right and left muscles of the back. Eight days after the first injection, blood was collected from the abdominal aorta and serum was separated. Thus, rat anti-DNP-As serum was obtained.

(2) PCA Reaction

The above-mentioned rat anti-DNP-As serum was diluted with physiological saline and the dilution was administered to male rats weighing about 120 to 200 g by intradermal injection into the back at a dose of 0.05 ml. After 45 hours, 0.1 g of each of the test preparations, the ointments and liniments obtained in the above-mentioned examples and comparative examples, was applied to the site of injection of anti-DNP-As serum in the same manner as in Test Example 1.

After 3 further hours, 0.5% Evans' blue solution in physiological saline containing the DNP-As antigen was administered by intravenous injection at a dose of 2.5 ml/kg to thereby induce the PCA reaction.

Thirty minutes later, the animals were sacrificed and the dye that had leaked out in the area of skin reaction was extracted by the method of Harada et al. (Journal of Pharmaceutics Pharmacology; 23, 218, 1971), namely by excising the reaction area of the skin, mincing the same and immersing the same in a mixed solution composed of 0.3% aqueous sodium sulfate solution and acetone (3:7, v/v) for not less than 48 hours. Then, the dye extracted was assayed by absorbance at 620 nm.

In a control run, the ointment base (Plastibase) alone was applied in lieu of the test preparation, then the same procedure was followed, and the dye extracted was assayed by absorbance.

From the results of determination of the amount (C) of the dye extracted from the site of application of the control and of the amount (D) of the dye extracted from the site of application of each test preparation, the dye-leakage inhibition percentage was calculated as follows:

Dye-leakage inhibition (%)=[(C−D)/C]×100

The results thus obtained are shown in Tables 1 to 3.

TEST EXAMPLE 3

Effect on Delayed Contact Dermal Hypersensitivity (type IV allergy) Reaction in Rats After the frank of 5-week-old Wistar rats was clipped of hairs, 20 μl of 20% 2,4-dinitrochlorobenzene (DNCB, Wako Pure Chemical Industries)-acetone was applied to the exposed skin area and allowed to sit for 2 weeks for sensitization.

After sensitization, the dorsal skin was clipped of hairs and 20 μl of 0.5% DNCB-acetone was applied to induce contact dermatitis.

Then, 0.1 g samples from the ointments or liniments obtained in the examples and comparative examples were respectively applied to the site of DNCB-induced dermatitis in the same manner as in Test Example 1.

Twenty-four hours after induction of dermatitis, the intensity of local erythema was evaluated using a chromameter (CR-200, Minolta).

In a control run, the ointment base (Plastibase) alone was applied in lieu of the test preparation and erythema intensity measurement was performed in the same manner.

From the results of measurement of the erythema intensity (E) at the site of application of the control and the erythema intensity (F) at the site of application of the test preparation, the erythema inhibition percentage was calculated as follows:

Erythema inhibition (%)=[(E−F)/E]×100

The results thus obtained are shown in Tables 1 to 3.

TEST EXAMPLE 4

Systemic Effect Evaluated in Terms of Body Weight Change

All the rats of the test groups and control group as used in Test Example 3 were weighed before and after testing and the possible systemic side effect was evaluated in terms of body weight changes. The results obtained are shown in Tables 1 to 3.

TEST EXAMPLE 5

Organoleptic Evaluation of Feel Upon Use

The ointments or liniments obtained in Examples 1 to 17 and 19 to 24 were each applied to the skin of five human subjects and evaluated for the feel upon application thereof according to the criteria mentioned below, and the mean value was calculated. The results are shown in Tables 1 and 2.

Evaluation criteria:
0: Significant stickiness and flow, no good feel.
1: Stickiness and flow noted.
2: No stickiness or flow, very good feel.

TABLE 1

| | | Composition (weight %) | | | | | | | Test Example | | | | |
|---|---|---|---|---|---|---|---|---|---|---|---|---|---|
| | | | Vitamin E | | | | | | 1 | 2 | 3 | 4 | 5 |
| | | Plastibase | Species | Content | Squalane | IPM | Dex | Pre | (%) | (%) | (%) | (g) | |
| Example | 1 | 96 | A | 2 | 2 | — | — | — | 25 | 18 | 27 | −2 | 2 |
| | 2 | 90 | A | 5 | 5 | — | — | — | 32 | 20 | 35 | 1 | 2 |
| | 3 | 80 | A | 10 | 10 | — | — | — | 39 | 24 | 41 | 1 | 2 |
| | 4 | 60 | A | 20 | 20 | — | — | — | 68 | 30 | 67 | 0 | 2 |
| | 5 | 50 | A | 40 | 10 | — | — | — | 72 | 32 | 74 | 0 | 2 |
| | 6 | 35 | A | 60 | 5 | — | — | — | 78 | 35 | 80 | −1 | 1 |
| | 7 | 25 | A | 70 | 5 | — | — | — | 80 | 40 | 85 | 0 | 0 |
| | 8 | 50 | A | 10 | 40 | — | — | — | 52 | 27 | 48 | −2 | 2 |
| | 9 | 35 | A | 5 | 60 | — | — | — | 59 | 29 | 52 | 0 | 1 |
| | 10 | 25 | A | 5 | 70 | — | — | — | 65 | 34 | 56 | 0 | 0 |
| | 11 | 70 | A | 10 | 10 | 10 | — | — | 48 | 28 | 50 | −1 | 2 |
| | 12 | 50 | A | 20 | 20 | 10 | — | — | 76 | 32 | 72 | 0 | 2 |
| | 13 | — | A | 90 | 10 | — | — | — | 82 | 40 | 86 | 0 | 0 |

TABLE 2

| | | Composition (weight %) | | | | | | | Test Example | | | | |
|---|---|---|---|---|---|---|---|---|---|---|---|---|---|
| | | | Vitamin E | | | | | | 1 | 2 | 3 | 4 | 5 |
| | | Plastibase | Species | Content | Squalane | IPM | Dex | Pre | (%) | (%) | (%) | (g) | |
| Example | 14 | — | A | 10 | 90 | — | — | — | 67 | 35 | 57 | 0 | 0 |
| | 15 | 20 | A | 20 | 20 | 40 | — | — | 83 | 38 | 75 | 0 | 1 |
| | 16 | — | A | 20 | 20 | 60 | — | — | 86 | 41 | 77 | 1 | 1 |
| | 17 | — | A | 10 | 10 | 80 | — | — | 62 | 34 | 60 | 1 | 0 |
| | 18 | 97.5 | A | 0.5 | 2 | — | — | — | — | — | — | — | — |
| | 19 | 60 | B | 20 | 20 | — | — | — | 70 | 35 | 71 | −1 | 2 |

TABLE 2-continued

| | | Composition (weight %) | | | | | | | Test Example | | | |
|---|---|---|---|---|---|---|---|---|---|---|---|---|
| | | | Vitamin E | | | | | | 1 | 2 | 3 | 4 |
| | | Plastibase | Species | Content | Squalane | IPM | Dex | Pre | (%) | (%) | (%) | (g) |
| | 20 | 50 | B | 40 | 10 | — | — | — | 73 | 38 | 73 | 1 |
| | 21 | 60 | C | 20 | 20 | — | — | — | 65 | 27 | 62 | 0 |
| | 22 | 50 | C | 40 | 10 | — | — | — | 70 | 30 | 71 | -1 |
| | 23 | 50 | B | 20 | 20 | 10 | — | — | 78 | 36 | 74 | 0 |
| | 24 | 50 | C | 20 | 20 | 10 | — | — | 70 | 30 | 68 | 1 |
| Control | | — | — | — | — | — | — | — | — | — | — | 0 |

TABLE 3

| | | Composition (weight %) | | | | | | | Test Example | | | |
|---|---|---|---|---|---|---|---|---|---|---|---|---|
| | | | Vitamin E | | | | | | 1 | 2 | 3 | 4 |
| | | Plastibase | Species | Content | Squalane | IPM | Dex | Pre | (%) | (%) | (%) | (g) |
| Comparative | 1 | 80 | A | — | 20 | — | — | — | 8 | 4 | 7 | 0 |
| Example | 2 | 60 | A | — | 40 | — | — | — | 10 | 5 | 9 | 0 |
| | 3 | 80 | A | 20 | — | — | — | — | 17 | 7 | 15 | -1 |
| | 4 | 60 | A | 40 | — | — | — | — | 20 | 8 | 17 | 1 |
| | 5 | 70 | A | — | 20 | 10 | — | — | 11 | 9 | 10 | 0 |
| | 6 | 50 | A | — | 40 | 10 | — | — | 14 | 10 | 15 | -1 |
| | 7 | 70 | A | 20 | — | 10 | — | — | 20 | 10 | 22 | 0 |
| | 8 | 50 | A | 40 | — | 10 | — | — | 23 | 12 | 24 | 0 |
| | 9 | 99.9 | A | — | — | — | 0.1 | — | 49 | 20 | 53 | -13 |
| | 10 | 99.5 | A | — | — | — | — | 0.5 | 52 | 23 | 48 | -12 |

In Tables 1 to 3, in the column "Species" below "Vitamin E", A stands for vitamin E acetate, B for vitamin E nicotinate, and C for vitamin E succinate. In the same tables, IPM stands for isopropyl myristate, Dex for dexamethasone, and Pre for prednisolone.

The ointments having low vitamin E and low squalane contents as obtained in Examples 1, 2 and 18 were further tested in the following manner.

TEST EXAMPLE 6

Effect of Repeated Administration on Delayed Contact Dermal Hypersensitivity (type IV allergy) Reaction in Rats After the frank of 5-week-old Wistar rats was clipped of hairs, 20 μl of 20% 2,4-dinitrochlorobenzene (DNCB, Wako Pure Chemical Industries)-acetone was applied to the exposed skin area and allowed to sit for 2 weeks for sensitization.

After sensitization, the back was clipped of hairs and 0.1 g samples from the ointments obtained in Examples 1, 2 and 18 were respectively applied once daily for 3 days prior to inducing contact dermatitis in the same manner as in Test Example 1. Three days after commencement of ointment application, 20 μl of 0.5% DNCB-acetone was applied to induce contact dermatitis.

Then, 0.1 g samples from ointments obtained in Examples 1, 2 and 18 were respectively applied to the site of DNCB-induced dermatitis in the same manner as in Test Example 1.

Twenty-four hours after induction of dermatitis, the intensity of local erythema was evaluated using a chromameter (CR-200, Minolta).

In a control run, the ointment base (Plastibase) alone was applied in lieu of the test preparation and erythema intensity measurement was performed in the same manner.

From the results of measurement of the erythema intensity (G) at the site of application of the control and the erythema intensity (H) at the site of application of the test preparation, erythema inhibition percentage was calculated as follows:

Erythema inhibition (%)=[(G−H)/G]×100

The results thus obtained are shown in Table 4.

TABLE 4

| | | Composition (weight %) | | | | Test Example |
|---|---|---|---|---|---|---|
| | | | Vitamin E | | | 6 |
| | | Plastibase | Species | Content | Squalane | (%) |
| Example | 1 | 96 | A | 2 | 2 | 44 |
| | 2 | 90 | A | 5 | 5 | 56 |
| | 18 | 97.5 | A | 0.5 | 2 | 38 |

Furthermore, the ointments obtained in Examples 3 to 5, 8, 11, 12 and 19 to 24 and Comparative Examples 9 and 10 were tested in the following manner.

In each test run, five rats were used and the results were shown in terms of mean value.

TEST EXAMPLE 7

Effect on Type III Allergy Model
(1) Preparation of Rabbit Anti-ovalbumin Serum

Rabbit anti-ovalbumin serum was prepared by the method of Eda et al. (Folia Pharmacologica Japonica; 66, 237, 1970).

Thus, ovalbumin (Sigma) was dissolved in physiological saline to a concentration of 2 mg/ml. An equivolume mixture (emulsion) of this solution and Freund's complete adjuvant (Difco) was used as an antigen preparation and 0.5 ml thereof was injected into the right and left gluteal muscles of each male rabbit (New Zealand white strain) four times at one-week intervals. Seven days after the last injection blood was collected from the carotid artery and serum was separated and recovered. Thus, rabbit anti-ovalbumin serum was obtained.

(2) Four-hour Heterologous Passive Cutaneous Anaphylaxis Reaction in Rats

The above rabbit anti-ovalbumin serum was 4-fold diluted with physiological saline and 0.05 ml of the dilution was intradermally injected into the back of each Wistar strain male rat weighing about 200 g. Then, 0.1 g of each of the ointments obtained in the above-mentioned examples and comparative examples was applied to the rat skin at the site of application of the antiserum in the same manner as in Test Example 1.

Then, 4 hours after antiserum injection, 0.5% Evans' blue solution in physiological saline containing 2 mg/ml of ovalbumin was intravenously administered at a dose of 2.5 ml/kg to thereby induce the PCA reaction.

The dye that had leaked out at the site of the thus-induced intracutaneous reaction was extracted and assayed by the method of Harada et al. (Journal of Pharmaceutics Pharmacology; 23, 218, 1971).

Thus, 30 minutes after Evans' blue administration, the animals were sacrificed. The skin excised from the reaction area was minced and immersed in a mixed solution of 0.3% aqueous solution of sodium sulfate and acetone (3:7, v/v) for not less than 48 hours for effecting extraction of the dye that had leaked out. The dye thus extracted was then assayed by absorbance at 620 nm.

In a control run, the ointment base (Plastibase) alone was applied in lieu of the test preparation. Thereafter, the same procedure was followed and the dye extracted was assayed by absorbance.

From the results of determination of the amount (I) of the dye extracted from the site of application of the control and of the amount (J) of the dye extracted from the site of application of each test preparation, the dye-leakage inhibition percentage was calculated as follows:

Dye-leakage inhibition (%)=[(I−J)/I]×100

The results thus obtained are shown in Tables 5 to 6.

TEST EXAMPLE 8

Effect on Delayed Dermal Hypersensitivity Reaction (tuberculin-induced type IV allergy reaction) in Rats The method of Kuriyama et al. (Folia Pharmacologica Japonica; 94, 113, 1989) was followed.

BCG (Bacillus Calmette-Guerin) (2.5 mg; Nihon BCG) was suspended in 1 ml of physiological saline. The suspension was heat-treated at 121° C. for 5 minutes and 0.2 ml thereof was injected into the peritoneal cavity of each 9-week-old Wistar rat.

Seven days after BCG injection, 200 μg of purified tuberculin (Nihon BCG) was dissolved in 1 ml of physiological saline and two 0.1-ml portions were respectively intradermally injected into two sites on the clipped back of the above rat.

Physiological saline, which was free of purified tuberculin, alone was also intradermally injected at another site on the clipped back in the same manner. Then, 0.1 g of each of the test preparations (ointments obtained in the above-mentioned examples and comparative examples) applied in the same manner as in Test Example 1 such that the ointment contacted the rat skin at one of the sites of injection of purified tuberculin.

As a control, the ointment base (Plastibase) alone was applied, in lieu of the test preparation, to the rat skin at the other tuberculin injection site in the same manner.

Twenty-four hours after said tuberculin injection, the diameter of the resulting erythema was measured and, from the results of measurement of the erythema diameter (K) at the control application site and of the erythema diameter (L) at the test preparation application site, the erythema inhibition percentage was calculated as follows:

Erythema inhibition (%)=[(K−L)/K]×100

The results obtained are shown in Tables 5 and 6.

TEST EXAMPLE 9

Effect on Solar Dermatitis (ultraviolet erythema)

The test preparations were examined for effect on ultraviolet-induced erythema by the method of Tsuji et al. (Oyo Yakuri (Pharmacometrics); 23, 567, 1982). Thus, the back of guinea pigs weighing 250 to 300 g was clipped of hairs. The skin of the back was then covered with a light-shielding cloth having three round holes with a diameter of 7 mm and ultraviolet irradiation was carried out from a distance of 20 cm for 30 seconds using a 1,000 watt ultraviolet lamp (Toshiba). Each (0.1 g) of the ointments obtained in the above-mentioned examples and comparative examples was applied as the test preparation to the site of ultraviolet-induced erythema 3 hours prior to irradiation and immediately after irradiation. Five hours after induction of dermatitis, the intensity of local erythema was evaluated using a chromameter (CR-200, Minolta).

As a control, the ointment base (Plastibase) alone was applied in the same manner in lieu of the test preparation and thereafter the erythema intensity was measured following the same procedure.

From the results of measurement of the erythema intensity (M) at the site of control application site and the erythema intensity (N) at the site of test preparation application, the erythema inhibition percentage was calculated as follows:

Erythema inhibition (%)=[(M−N)/M]×100

The results obtained are shown in Tables 5 and 6.

TEST EXAMPLE 10

Effect on Wound Healing

The ointments were evaluated for effect on wound healing by the method of Sakyo et al. (Oyo Yakuri; 43, 121, 1992).

The back of 5-week-old Wistar rats was shaved of hairs and using a surgical knife, a 30 mm-long incision was made along the median line under ether anesthesia. Immediately after incision, the wound was sutured in 3 equispaced positions.

Then, 0.2 g samples from the ointments obtained in the above examples and comparative examples were respectively spread on gauze (3-ply), 2.5 cm×5 cm, and applied to the wounded area and an occulusive dressing using an elastic adhesive bandage was applied for fixation.

The ointment-coated gauze was exchanged once/daily.

The suture was removed 3 days after commencement of the experiment. On day 6, the skin covering the whole wounded area was excised from each rat and 1 cm-wide skin strips parallel to the wound line (2 strips/rat) were prepared. Both ends of each strip were fixed to an NRM-3002D-L rheometer (Fudoh) and the tension force (g/cm) required for cutting the strip at the wound site was measured. The mean measured value for two strips was taken as the tension value for one sample.

As a control, the ointment base (Plastibase) alone was applied in the same manner in lieu of the test preparation and thereafter tension measurements were carried out following the same procedure.

The results obtained are shown in Tables 5 and 6.

When tested in the above manner, the external preparation for the treatment of dermatoses according to the first aspect of the present invention showed effects equivalent to those of external preparations containing an absorption enhancer or adrenocortical hormone and, unlike the adrenocortical hormone-containing external preparations, did not show any body weight loss due to side effects.

As compared with the single use of vitamin E or squalane, the combined use of both produced remarkable effects.

EXAMPLES 25 TO 47

Ointments were prepared by supplying white petrolatum (Maruishi Pharmaceutical), vitamin E acetate (Wako Pure Chemical Industries), vitamin E nicotinate (Wako Pure Chemical Industries), vitamin E succinate (Sigma), squalane (Wako Pure Chemical Industries), N-lauroylsarcosine (Nacalai Tesque), fumaric acid (Nacalai Tesque), cetyl lactate (Van-Dyk) and isopropyl myristate (Nacalai Tesque), in amounts specified below in Table 7, to a mortar, and kneading the mortar contents until the components other than white petrolatum were dissolved in the latter.

TABLE 5

| | | | Composition (weight %) | | | | | | Test Example | | | |
|---|---|---|---|---|---|---|---|---|---|---|---|---|
| | | | Vitamin E | | | | | | 7 | 8 | 9 | 10 |
| | | Plastibase | Species | Content | Squalane | IPM | Dex | Pre | (%) | (%) | (%) | (g/cm) |
| Example | 3 | 80 | A | 10 | 10 | — | — | — | 19 | 16 | 30 | 230 |
| | 4 | 60 | A | 20 | 20 | — | — | — | 25 | 21 | 37 | 248 |
| | 5 | 50 | A | 40 | 10 | — | — | — | 30 | 29 | 43 | 263 |
| | 8 | 50 | A | 10 | 40 | — | — | — | 29 | 27 | 39 | 251 |
| | 11 | 70 | A | 10 | 10 | 10 | — | — | 23 | 21 | 36 | 246 |
| | 12 | 50 | A | 20 | 20 | 10 | — | — | 30 | 28 | 42 | 261 |

TABLE 6

| | | | Composition (weight %) | | | | | | Test Example | | | |
|---|---|---|---|---|---|---|---|---|---|---|---|---|
| | | | Vitamin E | | | | | | 7 | 8 | 9 | 10 |
| | | Plastibase | Species | Content | Squalane | IPM | Dex | Pre | (%) | (%) | (%) | (g/cm) |
| Example | 19 | 60 | B | 20 | 20 | — | — | — | 30 | 20 | 36 | 247 |
| | 20 | 50 | B | 40 | 10 | — | — | — | 35 | 28 | 45 | 264 |
| | 21 | 60 | C | 20 | 20 | — | — | — | 23 | 18 | 35 | 240 |
| | 22 | 50 | C | 40 | 10 | — | — | — | 28 | 25 | 39 | 255 |
| | 23 | 50 | B | 20 | 20 | 10 | — | — | 35 | 29 | 43 | 263 |
| | 24 | 50 | C | 20 | 20 | 10 | — | — | 28 | 26 | 40 | 258 |
| Comparative | 9 | 99.9 | — | — | — | — | 0.1 | — | 28 | 23 | 17 | — |
| Example | 10 | 99.5 | — | — | — | — | — | 0.5 | 25 | 20 | 13 | — |
| Control | | — | — | — | — | — | — | — | — | — | — | 175 |

TABLE 7

| | | White petrolatum | Vitamin E Species | Vitamin E Content | Squalane | LS | Fumaric acid | Cetyl lactate | IPM |
|---|---|---|---|---|---|---|---|---|---|
| Example | 25 | 79 | A | 10 | 10 | 1 | — | — | — |
| | 26 | 59 | A | 20 | 20 | 1 | — | — | — |
| | 27 | 19 | A | 40 | 40 | 1 | — | — | — |
| | 28 | 79 | A | 10 | 10 | — | 1 | — | — |
| | 29 | 59 | A | 20 | 20 | — | 1 | — | — |
| | 30 | 19 | A | 40 | 40 | — | 1 | — | — |
| | 31 | 79 | A | 10 | 10 | — | — | 1 | — |
| | 32 | 59 | A | 20 | 20 | — | — | 1 | — |
| | 33 | 19 | A | 40 | 40 | — | — | 1 | — |
| | 34 | 70 | A | 10 | 10 | — | — | — | 10 |
| | 35 | 50 | A | 20 | 20 | — | — | — | 10 |
| | 36 | 10 | A | 40 | 40 | — | — | — | 10 |
| | 37 | 80 | A | 10 | 10 | — | — | — | — |
| | 38 | 60 | A | 20 | 20 | — | — | — | — |
| | 39 | 20 | A | 40 | 40 | — | — | — | — |
| | 40 | 59 | B | 20 | 20 | 1 | — | — | — |
| | 41 | 59 | B | 20 | 20 | — | 1 | — | — |
| | 42 | 59 | B | 20 | 20 | — | — | 1 | — |
| | 43 | 50 | B | 20 | 20 | — | — | — | 10 |
| | 44 | 59 | C | 20 | 20 | 1 | — | — | — |
| | 45 | 59 | C | 20 | 20 | — | 1 | — | — |
| | 46 | 59 | C | 20 | 20 | — | — | 1 | — |
| | 47 | 50 | C | 20 | 20 | — | — | — | 10 |

In Table 7, in the column "Species" under "Vitamin E", A stands for vitamin E acetate, B for vitamin E nicotinate, and C for vitamin E succinate. In the same table, IPM stands for isopropyl myristate, and LS for N-lauroylsarcosine.

EXAMPLE 48

Vitamin E acetate (40% by weight; Wako Pure Chemical Industries), 40% by weight of squalane (Wako Pure Chemical Industries) and 20% by weight of olive oil were supplied to a beaker and the contents were stirred until homogeneous dissolution of the whole, to give a liniment.

EXAMPLE 49

Vitamin E acetate (20% by weight; Wako Pure Chemical Industries), 20% by weight of squalane (Wako Pure Chemical Industries) and 60% by weight of olive oil were supplied to a beaker and the contents were stirred until homogeneous dissolution of the whole, to give a liniment.

EXAMPLE 50

Vitamin E nicotinate (40% by weight; Wako Pure Chemical Industries), 40% by weight of squalane (Wako Pure Chemical Industries) and 20% by weight of olive oil were supplied to a beaker and the contents were stirred until homogeneous dissolution of the whole, to give a liniment.

EXAMPLE 51

Vitamin E succinate (40% by weight; Sigma), 40% by weight of squalane (Wako Pure Chemical Industries) and 20% by weight of olive oil were supplied to a beaker and the contents were stirred until homogeneous dissolution of the whole, to give a liniment.

EXAMPLE 52

[Synthesis of acrylic adhesive]

A separable flask equipped with a stirrer and a condenser was charged with 301.1 weight parts of 2-ethylhexyl methacrylate, 34.9 weight parts of 2-ethylhexyl acrylate, 48.3 weight parts of dodecyl methacrylate, 0.0384 weight part of 1,6-hexaneglycol dimethacrylate and 256.0 weight parts of ethyl acetate, and the mixture was heated to 70° C. with stirring and nitrogen substitution.

A solution of 2.0 weight parts of lauroyl peroxide in 10.0 weight parts of cyclohexane was divided into 10 aliquots. One aliquot was added to the separable flask to thereby initiate the polymerization. Starting at 5 hours after initiation of the polymerization, the remaining 9 aliquots were added one by one at 1-hour intervals. After completion of the addition, the reaction was further continued for 19 hours. For viscosity adjustment, five 27 weight part portions of ethyl acetate were added one by one at 5-hour intervals after initiation of the reaction.

After completion of the reaction, the reaction mixture was cooled and ethyl acetate was further added to give an adhesive solution with a solid content of 50% by weight.

[Production of tape-form preparation]

The above adhesive solution (120 weight parts), 20 weight parts of vitamin E acetate (Wako Pure Chemical Industries) and 20 weight parts of squalane (Wako Pure Chemical Industries) were supplied to a dissolver-type high-speed mixer and homogeneously blended to give a mixed solution.

The thus-obtained mixed solution was applied to a silicone-treated polyethylene terephthalate film (38 μm thick) and then dried at 60° C. for 30 minutes to give a 80-μm-thick adhesive layer.

The above adhesive layer was then transferred onto the ethylene-vinyl acetate copolymer layer of a 34 μm thick polyethylene terephthalate/ethylene-vinyl acetate copolymer laminate film, to give a tape-form preparation.

EXAMPLE 53

A tape-form preparation was produced by following the procedure of Example 52 except that the adhesive solution was used in an amount of 180 weight parts, vitamin E acetate in an amount of 5 weight parts and squalane in an amount of 5 weight parts.

EXAMPLE 54

A tape-form preparation was produced by following the procedure of Example 52 except that the adhesive solution was used in an amount of 120 weight parts, 20 weight parts of vitamin E nicotinate (Wako Pure Chemical Industries) was used in lieu of 20 weight parts of vitamin E acetate, and squalane was used in an amount of 20 weight parts.

EXAMPLE 55

A tape-form preparation was produced by following the procedure of Example 52 except that the adhesive solution was used in an amount of 120 weight parts, 20 weight parts of vitamin E succinate (Sigma) was used in lieu of 20 weight parts of vitamin E acetate, and squalane was used in an amount of 20 weight parts.

EXAMPLES 56 TO 79 AND COMPARATIVE EXAMPLES 11 TO 20

Ointments were prepared by supplying Plastibase (Taisho Pharmaceutical), dexamethasone (Wako Pure Chemical Industries), prednisolone (Wako Pure Chemical Industries), triamcinolone acetonide (Wako Pure Chemical Industries), vitamin E acetate (Wako Pure Chemical Industries) and squalane (Wako Pure Chemical Industries), in amounts specified below in Tables 8 and 9, to a mortar, and kneading the mortar contents until the components other than Plastibase were dissolved in the latter.

In Tables 8 and 9, Tac stands for triamcinolone acetonide.

TABLE 8

| | Composition (weight %) | | | | | |
|---|---|---|---|---|---|---|
| Example | Plastibase | Dexamethasone | Prednisolone | Tac | Vitamin E | Squalane |
| 56 | 84.400 | 0.1   | —     | —     | 0.5 | 15 |
| 57 | 64.900 | 0.1   | —     | —     | 20  | 15 |
| 58 | 84.490 | 0.01  | —     | —     | 0.5 | 15 |
| 59 | 64.990 | 0.01  | —     | —     | 20  | 15 |
| 60 | 84.499 | 0.001 | —     | —     | 0.5 | 15 |
| 61 | 64.999 | 0.001 | —     | —     | 20  | 15 |
| 62 | 69.499 | 0.001 | —     | —     | 0.5 | 30 |
| 63 | 49.999 | 0.001 | —     | —     | 20  | 30 |
| 64 | 84.000 | —     | 0.5   | —     | 0.5 | 15 |
| 65 | 64.500 | —     | 0.5   | —     | 20  | 15 |
| 66 | 84.450 | —     | 0.05  | —     | 0.5 | 15 |
| 67 | 64.950 | —     | 0.05  | —     | 20  | 15 |
| 68 | 84.490 | —     | 0.01  | —     | 0.5 | 15 |
| 69 | 64.990 | —     | 0.01  | —     | 20  | 15 |
| 70 | 84.495 | —     | 0.005 | —     | 0.5 | 15 |
| 71 | 64.995 | —     | 0.005 | —     | 20  | 15 |
| 72 | 69.495 | —     | 0.005 | —     | 0.5 | 30 |
| 73 | 49.995 | —     | 0.005 | —     | 20  | 30 |
| 74 | 84.400 | —     | —     | 0.1   | 0.5 | 15 |
| 75 | 64.900 | —     | —     | 0.1   | 20  | 15 |
| 76 | 84.490 | —     | —     | 0.01  | 0.5 | 15 |
| 77 | 64.990 | —     | —     | 0.01  | 20  | 15 |
| 78 | 84.499 | —     | —     | 0.001 | 0.5 | 15 |
| 79 | 64.999 | —     | —     | 0.001 | 20  | 15 |

TABLE 9

| | Composition (weight %) | | | | | |
|---|---|---|---|---|---|---|
| Comparative Example | Plastibase | Dexamethasone | Prednisolone | Tac | Vitamin E | Squalane |
| 11 | 99.900 | 0.1   | —     | —     | — | — |
| 12 | 99.990 | 0.01  | —     | —     | — | — |
| 13 | 99.999 | 0.001 | —     | —     | — | — |
| 14 | 99.500 | —     | 0.5   | —     | — | — |
| 15 | 99.950 | —     | 0.05  | —     | — | — |
| 16 | 99.990 | —     | 0.01  | —     | — | — |
| 17 | 99.995 | —     | 0.005 | —     | — | — |
| 18 | 99.900 | —     | —     | 0.1   | — | — |
| 19 | 99.990 | —     | —     | 0.01  | — | — |
| 20 | 99.999 | —     | —     | 0.001 | — | — |

The thus-obtained ointments were tested as in Test Examples 1 to 5, 7 and 9 and further tested as described below in Test Example 11. In Test Examples 1 to 4, 7 and 11, each ointment was evaluated using 5 rats and the results were expressed in terms of mean value. In Test Example 9, 5 guinea pigs were used for each ointment and the results were expressed in terms of mean value. The results obtained are shown in Tables 10 and 11.

TEST EXAMPLE 11

Effect on Delayed Dermal Hypersensitivity Reaction (tuberculin reaction) in Rats The method of Kuriyama et al. (Folia Pharmacologica Japonica; 94, 113, 1989) was used.

Thus, 2.5 mg of BCG (Bacillus Calmette-Geurin; Nihon BCG) was suspended in 1 ml of physiological saline, the suspension was heat-treated at 121° C. for 5 minutes and a 0.2-ml portion thereof was injected into the peritoneal cavity of each 9-week-old Wistar rat.

Seven days after BCG injection, 0.1 ml of a solution prepared by dissolving 200 μg of purified tuberculin (Nihon BCG) in 1 ml of physiological saline was intradermally injected into two sites on the clipped back the above rat. Physiological saline, which was free of purified tuberculin, alone was intradermally injected at another site on the clipped back in the same manner. Then, 0.1 g of each of the test preparations obtained in the above-mentioned examples and comparative examples was applied in the same manner as in Test Example 1 so that the ointment came into contact with one of the purified tuberculin injection sites on the rat skin.

As a control, the ointment base (Plastibase) alone was applied in the same manner to the other tuberculin injection site on the rat skin.

Twenty-four hours after tuberculin injection, the color tone of the resulting erythema was measured using a chromameter. From the results of measurement of the color difference value (K) for the erythema at the control application site and of the color difference value (L) for the erythema at the test preparation application site, the erythema inhibition percentage was calculated as follows:

Erythema inhibition (%)=[(K−L)/K]×100

The results obtained are shown in Tables 10 and 11.

TABLE 10

| | | Test Example | | | | | | | |
|---|---|---|---|---|---|---|---|---|---|
| | | 1 (%) | 2 (%) | 3 (%) | 4 (g) | 5 | 7 (%) | 9 (%) | 11 (%) |
| Example | 56 | 65.4 | 50.9 | 64.1 | -5 | 2 | — | 31.6 | 42.8 |
| | 57 | 70.1 | 61.2 | 68.4 | -4 | 2 | — | 40.3 | 50.3 |
| | 58 | 37.5 | 22.8 | 42.0 | -1 | 2 | 35.6 | — | 23.4 |
| | 59 | 47.3 | 31.2 | 52.1 | 0 | 2 | 44.8 | — | 30.9 |
| | 60 | 15.3 | 5.9 | 10.4 | 1 | 2 | — | — | 9.6 |
| | 61 | 27.1 | 15.4 | 24.1 | 2 | 2 | — | — | 14.8 |
| | 62 | 18.2 | 7.9 | 13.2 | 2 | 2 | — | — | 12.1 |
| | 63 | 30.9 | 21.4 | 27.3 | 2 | 0 | — | — | 18.8 |
| | 64 | 65.8 | 49.8 | 64.6 | -6 | 2 | — | 31.0 | 44.1 |
| | 65 | 69.4 | 60.3 | 68.5 | -6 | 2 | — | 39.2 | 48.3 |
| | 66 | 37.6 | 30.4 | 37.1 | -4 | 2 | 34.1 | — | 20.6 |
| | 67 | 49.8 | 36.8 | 47.1 | -4 | 2 | 42.9 | — | 30.0 |
| | 68 | 25.1 | 21.8 | 23.1 | -2 | 2 | — | — | 13.4 |
| | 69 | 38.3 | 30.4 | 39.6 | -1 | 2 | — | — | 20.6 |
| | 70 | 14.9 | 5.7 | 9.8 | 1 | 2 | — | — | 7.9 |
| | 71 | 26.9 | 14.6 | 23.6 | 1 | 2 | — | — | 14.2 |
| | 72 | 17.8 | 7.0 | 12.3 | 2 | 2 | — | — | 11.0 |
| | 73 | 30.1 | 19.8 | 26.1 | 2 | 0 | — | — | 17.4 |
| | 74 | 64.2 | 50.3 | 63.9 | -5 | 2 | — | 31.4 | 43.2 |
| | 75 | 70.3 | 60.8 | 68.3 | -5 | 2 | — | 40.0 | 51.0 |
| | 76 | 37.8 | 22.4 | 42.3 | -3 | 2 | 35.2 | — | 23.6 |
| | 77 | 47.0 | 31.1 | 51.6 | -2 | 2 | 44.5 | — | 29.8 |
| | 78 | 15.4 | 5.4 | 10.3 | 2 | 2 | — | — | 9.4 |
| | 79 | 26.9 | 15.3 | 24.3 | 2 | 2 | — | — | 14.5 |
| Control | | — | — | — | 0 | — | — | — | — |

TABLE 11

| | | Text Example | | | | | | | |
|---|---|---|---|---|---|---|---|---|---|
| | | 1 (%) | 2 (%) | 3 (%) | 4 (g) | 5 | 7 (%) | 9 (%) | 11 (%) |
| Comparative | 11 | 50.6 | 42.8 | 53.1 | -5 | 2 | 50.1 | 29.2 | 39.1 |
| Example | 12 | 26.3 | 21.1 | 27.4 | -4 | 2 | 30.1 | 5.3 | 18.7 |
| | 13 | 1.2 | 0.8 | 0.7 | 0 | 2 | — | — | 0.3 |
| | 14 | 52.1 | 43.6 | 55.2 | -6 | 2 | 48.2 | 27.3 | 41.0 |
| | 15 | 27.2 | 22.1 | 26.4 | -4 | 2 | 28.5 | 4.0 | 16.8 |
| | 16 | 9.4 | 7.6 | 8.6 | -2 | 2 | — | — | 6.3 |
| | 17 | 0.8 | 0.5 | 0.5 | 0 | 2 | — | — | 0.2 |
| | 18 | 51.8 | 42.7 | 54.8 | -5 | 2 | 49.8 | 28.5 | 40.8 |
| | 19 | 23.1 | 20.0 | 26.1 | -3 | 2 | 29.5 | 5.1 | 13.1 |
| | 20 | 0.7 | 0.6 | 0.8 | 0 | 2 | — | — | 0.2 |

The results shown in Tables 10 and 11 indicate that the external preparation for the treatment of dermatoses according to the second aspect of the present invention have high curative effects on dermatoses as compared with the conventional adrenocortical hormone-containing external preparations. Thus, it was proved that the second aspect of the present invention provides highly safe external preparations for dermatoses which are widely efficacious against dermatoses even when the adrenocortical hormone content is low.

EXAMPLES 80 TO 109

Ointments were prepared by supplying Plastibase (Taisho Pharmaceutical), white petrolatum (maruishi Pharmaceutical), amcinonide (Sigma), diflucortolone valerate (Sigma), dexamethasone (Wako Pure Chemical Industries), dexamethasone acetate (Sigma), halcinonide (Sigma), hydrocortisone acetate (Wako Pure Chemical Industries), fluocinonide (Sigma), flumethasone pivalate (Sigma), prednisolone (Wako Pure Chemical Industries), betamethasone dipropionate (Wako Pure Chemical Industries), betamethasone valerate (Wako Pure Chemical Industries), vitamin E acetate (Wako Pure Chemical Industries), squalane (Wako Pure Chemical Industries), isopropyl myristate (Nacalai Tesque) and N-lauroylsarcosine (Nacalai Tesque), in amounts specified below in Tables 12 and 13, to a mortar, and kneading the mortar contents until the components other than the base (Plastibase or white petrolatum) were dissolved in the latter.

In Tables 12 and 13, in the column "Species" below "Base", A stands for Plastibase and B for white petrolatum. In the column "Species" below "Adrenocortical hormone", F stands for amcinonide, G for diflucortolone valerate, H for dexamethasone, I for dexamethasone acetate, J for halcinonide, K for hydrocortisone acetate, L for fluocinonide, M for flumethasone pivalate, N for prednisolone, O for betamethasone dipropionate and P for betamethasone valerate. In the column "IPM", IPM stands for isopropyl myristate and, in the column "LS", LS stands for N-lauroylsarcosine.

TABLE 12

| | | Composition (weight %) | | | | | | | |
|---|---|---|---|---|---|---|---|---|---|
| | | Base | | Adrenocortical hormone | | | | | |
| | | Species | Content | Species | Content | Vitamin E | Squalane | IPM | LS |
| Example | 80 | A | 84.498 | F | 0.002 | 0.5 | 15 | — | — |
| | 81 | A | 69.999 | F | 0.001 | 10 | 20 | — | — |
| | 82 | A | 79.998 | G | 0.002 | 5 | 15 | — | — |
| | 83 | A | 54.998 | G | 0.002 | 15 | 30 | — | — |
| | 84 | A | 84.996 | H | 0.004 | 5 | 10 | — | — |
| | 85 | A | 69.999 | H | 0.001 | 20 | 10 | — | — |
| | 86 | A | 88.499 | H | 0.001 | 0.5 | 10 | 1 | — |
| | 87 | A | 68.999 | H | 0.001 | 20 | 10 | 1 | — |
| | 88 | A | 89.399 | H | 0.001 | 0.5 | 10 | — | 0.1 |
| | 89 | A | 69.899 | H | 0.001 | 20 | 10 | — | 0.1 |
| | 90 | A | 79.990 | I | 0.010 | 5 | 15 | — | — |
| | 91 | A | 24.999 | I | 0.001 | 30 | 45 | — | — |
| | 92 | A | 79.990 | J | 0.010 | 5 | 15 | — | — |

TABLE 12-continued

| | | Base | | Adrenocortical hormone | | | | | |
|---|---|---|---|---|---|---|---|---|---|
| | | Species | Content | Species | Content | Vitamin E | Squalane | IPM | LS |
| | 93 | A | 54.999 | J | 0.001 | 30 | 15 | — | — |
| | 94 | B | 68.500 | K | 1.000 | 0.5 | 30 | — | — |
| | 95 | B | 49.900 | K | 0.100 | 20 | 30 | — | — |
| | 96 | B | 54.998 | L | 0.002 | 15 | 30 | — | — |
| | 97 | B | 69.999 | L | 0.001 | 15 | 15 | — | — |
| | 98 | B | 83.999 | M | 0.001 | 1 | 15 | — | — |
| | 99 | B | 44.999 | M | 0.001 | 40 | 15 | — | — |
| | 100 | B | 84.490 | N | 0.010 | 0.5 | 15 | — | — |
| | 101 | B | 64.990 | N | 0.010 | 20 | 15 | — | — |

TABLE 13

| | | Base | | Adrenocortical hormone | | | | | |
|---|---|---|---|---|---|---|---|---|---|
| | | Species | Content | Species | Content | Vitamin E | Squalane | IPM | LS |
| Example | 102 | B | 83.499 | N | 0.001 | 0.5 | 15 | 1 | — |
| | 103 | B | 63.999 | N | 0.001 | 20 | 15 | 1 | — |
| | 104 | B | 84.399 | N | 0.001 | 0.5 | 15 | — | 0.1 |
| | 105 | B | 64.899 | N | 0.001 | 20 | 15 | — | 0.1 |
| | 106 | B | 83.497 | O | 0.003 | 1.5 | 15 | — | — |
| | 107 | B | 64.999 | O | 0.001 | 5 | 30 | — | — |
| | 108 | B | 83.498 | P | 0.002 | 1.5 | 15 | — | — |
| | 109 | B | 69.999 | P | 0.001 | 15 | 15 | — | — |
| | 110 | C | 84.498 | H | 0.002 | 0.5 | 15 | — | — |
| | 111 | D | 49.999 | H | 0.001 | 20 | 30 | — | — |
| | 112 | C | 54.490 | I | 0.01 | 0.5 | 45 | — | — |
| | 113 | D | 29.995 | I | 0.005 | 20 | 50 | — | — |
| | 114 | C | 84.000 | K | 0.5 | 0.5 | 15 | — | — |
| | 115 | D | 49.900 | K | 0.1 | 20 | 30 | — | — |
| | 116 | C | 83.490 | N | 0.01 | 1.5 | 15 | — | — |
| | 117 | E | 68.480 | N | 0.02 | 1.5 | 30 | — | — |
| | 118 | C | 69.995 | P | 0.005 | 15 | 15 | — | — |
| | 119 | E | 54.999 | P | 0.001 | 30 | 15 | — | — |

EXAMPLES 110 TO 146

Liniments were prepared by supplying olive oil (Maruishi Pharmaceutical), sesame oil (Maruishi Pharmaceutical), peanut oil (Maruishi Pharmaceutical), dexamethasone (Wako Pure Chemical Industries), dexamethasone acetate (Sigma), hydrocortisone acetate (Wako Pure Chemical Industries), prednisolone (Wako Pure Chemical Industries), betamethasone valerate (Wako Pure Chemical Industries), vitamin E acetate (Wako Pure Chemical Industries) and squalane (Wako Pure Chemical Industries), in amounts specified below in Table 13 (shown above) and Table 14, to a mortar, and stirring the mortar contents until the base (olive oil, sesame oil or peanut oil) and other additives were homogeneously mixed up.

In Tables 13 and 14, in the column "Species" below "Base", C stands for olive oil, D for sesame oil and E for peanut oil. In the column "Species" below "Adrenocortical hormone", H, I, K, N and P are the same as in Tables 12 and 13.

TABLE 14

| | | Base | Adrenocortical hormone | | | | | |
|---|---|---|---|---|---|---|---|---|
| | | Base | Species | Content | Vitamin E | Squalane | IPM | LS |
| Example | 120 | — | N | 0.01 | 0.5 | 99.49 | — | — |
| | 121 | — | N | 0.01 | 5 | 94.99 | — | — |
| | 122 | — | N | 0.01 | 15 | 84.99 | — | — |
| | 123 | — | N | 0.01 | 30 | 69.99 | — | — |
| | 124 | — | N | 0.01 | 45 | 54.99 | — | — |
| | 125 | — | N | 0.01 | 60 | 39.99 | — | — |
| | 126 | — | N | 0.01 | 75 | 24.99 | — | — |
| | 127 | — | N | 0.01 | 90 | 9.99 | — | — |
| | 128 | — | N | 0.01 | 98 | 1.99 | — | — |
| | 129 | — | I | 0.005 | 0.5 | 99.495 | — | — |
| | 130 | — | I | 0.005 | 5 | 94.995 | — | — |
| | 131 | — | I | 0.005 | 15 | 84.995 | — | — |
| | 132 | — | I | 0.005 | 30 | 69.995 | — | — |
| | 133 | — | I | 0.005 | 45 | 54.995 | — | — |

TABLE 14-continued

| | Composition (weight %) | | | | | |
|---|---|---|---|---|---|---|
| | Adrenocortical hormone | | | | | |
| Base | Species | Content | Vitamin E | Squalane | IPM | LS |
| 134 | — | I | 0.005 | 60 | 39.995 | — | — |
| 135 | — | I | 0.005 | 75 | 24.995 | — | — |
| 136 | — | I | 0.005 | 90 | 9.995 | — | — |
| 137 | — | I | 0.005 | 98 | 1.995 | — | — |
| 138 | — | P | 0.001 | 0.5 | 99.499 | — | — |
| 139 | — | P | 0.001 | 5 | 94.999 | — | — |
| 140 | — | P | 0.001 | 15 | 84.999 | — | — |
| 141 | — | P | 0.001 | 30 | 69.999 | — | — |
| 142 | — | P | 0.001 | 45 | 54.999 | — | — |
| 143 | — | P | 0.001 | 60 | 39.999 | — | — |
| 144 | — | P | 0.001 | 75 | 24.999 | — | — |
| 145 | — | P | 0.001 | 90 | 9.999 | — | — |
| 146 | — | P | 0.001 | 98 | 1.999 | — | — |

EXAMPLE 147

[Synthesis of acrylic adhesive]

A separable flask equipped with a stirrer and a condenser was charged with 301.1 weight parts of 2-ethylhexyl methacrylate, 34.9 weight parts of 2-ethylhexyl acrylate, 48.3 weight parts of dodecyl methacrylate, 0.0384 weight part of 1,6-hexaneglycol dimethacrylate and 256.0 weight parts of ethyl acetate, and the flask contents were heated to 70° C. with stirring and nitrogen substitution.

A solution of 2.0 weight parts of lauroyl peroxide in 10.0 weight parts of cyclohexane was divided into 10 aliquots. One aliquot was added to the separable flask to thereby initiate the polymerization. Starting at 5 hours after initiation of the polymerization, the remaining 9 aliquots were added one by one at 1-hour intervals. After completion of the addition, the reaction was further carried out for 19 hours. For viscosity adjustment, five 27 weight part portions of ethyl acetate were added one by one at 5-hour intervals after initiation of the reaction.

After completion of the reaction, the reaction mixture was cooled and ethyl acetate was further added to give an adhesive solution with a solid content of 50% by weight.
[Production of tape-form preparation]

The above adhesive solution (168.98 weight parts), 0.01 weight part of prednisolone (Wako Pure Chemical Industries), 0.5 weight part of vitamin E acetate (Wako Pure Chemical Industries) and 15 weight parts of squalane (Wako Pure Chemical Industries) were supplied to a dissolver-type high-speed mixer and homogeneously blended to give a mixed solution.

The thus-obtained mixed solution was applied to a silicone-treated polyethylene terephthalate film (38 μm thick) and then dried at 60° C. for 30 minutes to give a 80-μm-thick adhesive layer.

The above adhesive layer was then transferred onto the ethylene-vinyl acetate copolymer layer of a 34 μm thick polyethylene terephthalate/ethylene-vinyl acetate copolymer laminate film, to give a tape-form preparation.

EXAMPLE 148

[Synthesis of acrylic adhesive]

The procedure of Example 147 was followed to give an adhesive solution with a solid content of 50% by weight.
[Production of tape-form preparation]

A tape-form preparation was obtained in the same manner as in Example 147 except that 139.98 weight parts of the above adhesive solution, 0.01 weight part of prednisolone (Wako Pure Chemical Industries), 15 weight parts of vitamin E acetate (Wako Pure Chemical Industries) and 15 weight parts of squalane (Wako Pure Chemical Industries) were used.

EXAMPLE 149

[Synthesis of acrylic adhesive]

The procedure of Example 147 was followed to give an adhesive solution with a solid content of 50% by weight.
[Production of tape-form preparation]

A tape-form preparation was obtained in the same manner as in Example 147 except that 166.99 weight parts of the above adhesive solution, 0.005 weight part of dexamethasone (Wako Pure Chemical Industries), 1.5 weight parts of vitamin E acetate (Wako Pure Chemical Industries) and 15 weight parts of squalane (Wako Pure Chemical Industries) were used.

EXAMPLES 150 TO 167 AND COMPARATIVE EXAMPLES 21 TO 24

Ointments were prepared by supplying Plastibase (Taisho Pharmaceutical), bufexamac (Sigma), indomethacin (Sigma), vitamin E acetate (Wako Pure Chemical Industries), squalane (Wako Pure Chemical Industries), squalene (Sigma), isopropyl myristate (Nacalai Tesque), dexamethasone (Wako Pure Chemical Industries) and prednisolone (Wako Pure Chemical Industries), in amounts specified below in Table 15, to a mortar, and kneading the mortar contents until the components other than Plastibase were dissolved in the latter.

TABLE 15

| | | Composition (weight %) | | | | | | | | |
|---|---|---|---|---|---|---|---|---|---|---|
| | | Plastibase | Bufexamac | Indomethacin | Vitamin E | Squalane | Squalene | Isopropyl myristate | Dexamethasone | Prednisolone |
| Example | 150 | 79.5 | 5 | — | 0.5 | 15 | — | — | — | — |
| | 151 | 60 | 5 | — | 20 | 15 | — | — | — | — |
| | 152 | 45 | 5 | — | 20 | 30 | — | — | — | — |
| | 153 | 30 | 5 | — | 50 | 15 | — | — | — | — |
| | 154 | 15 | 5 | — | 50 | 30 | — | — | — | — |
| | 155 | 69.5 | 5 | — | 0.5 | 15 | — | 10 | — | — |
| | 156 | 50 | 5 | — | 20 | 15 | — | 10 | — | — |
| | 157 | 35 | 5 | — | 20 | 30 | — | 10 | — | — |
| | 158 | 64 | — | 1 | 20 | 15 | — | — | — | — |
| | 159 | 54 | — | 1 | 20 | 15 | — | 10 | — | — |
| | 160 | 70 | 5 | — | 20 | — | 5 | — | — | — |
| | 161 | 45 | 5 | — | 20 | — | 30 | — | — | — |

TABLE 15-continued

| | | Composition (weight %) | | | | | | | | |
|---|---|---|---|---|---|---|---|---|---|---|
| | | Plastibase | Bufexamac | Indomethacin | Vitamin E | Squalane | Squalene | Isopropyl myristate | Dexamethasone | Prednisolone |
| | 162 | 55 | 5 | — | 20 | 15 | 5 | — | — | — |
| | 163 | 15 | 5 | — | 20 | 30 | 30 | — | — | — |
| | 164 | 74 | — | 1 | 20 | — | 5 | — | — | — |
| | 165 | 49 | — | 1 | 20 | — | 30 | — | — | — |
| | 166 | 59 | — | 1 | 20 | 15 | 5 | — | — | — |
| | 167 | 19 | — | 1 | 20 | 30 | 30 | — | — | — |
| Comparative | 21 | 95 | 5 | — | — | — | — | — | — | — |
| Example | 22 | 99 | — | 1 | — | — | — | — | — | — |
| | 23 | 99.9 | — | — | — | — | — | — | 0.1 | — |
| | 24 | 99.5 | — | — | — | — | — | — | — | 0.5 |

The thus-obtained ointments were tested as in Test Examples 1 to 4, 7 and 9 to 11. In Test Examples 1 to 4, 7, 10 and 1, each ointment was tested using 5 rats and the results were expressed in terms of mean value. In Test Example 9, each ointment was tested using 5 guinea pigs and the results were expressed in terms of mean value. The results thus obtained are shown in Table 16.

TABLE 16

| | Test Example | | | | | | | |
|---|---|---|---|---|---|---|---|---|
| | 1 (%) | 2 (%) | 3 (%) | 4 (g) | 7 (%) | 9 (%) | 10 (g/cm) | 11 (%) |
| Example | | | | | | | | |
| 150 | 21.6 | 18.2 | 24.6 | 2 | — | — | — | 10.1 |
| 151 | 83.8 | 29.4 | 84.1 | 1 | 19.3 | 66.4 | 261 | 23.7 |
| 152 | 86.9 | 32.8 | 87.9 | 3 | — | — | — | 27.5 |
| 153 | 83.8 | 33.3 | 87.9 | 0 | — | — | — | 31.2 |
| 154 | 84.8 | 37.3 | 88.1 | 1 | — | — | — | 32.5 |
| 155 | 26.1 | 23.3 | 24.5 | 2 | — | — | — | 20.8 |
| 156 | 87.8 | 44.9 | 91.2 | 1 | 21.1 | 75.4 | 271 | 31.9 |
| 157 | 89.8 | 46.3 | 86.6 | 1 | — | — | — | 36.2 |
| 158 | 81.4 | 27.8 | 78.6 | 0 | 14.8 | 68.1 | 233 | 31.9 |
| 159 | 80.2 | 39.8 | 86.2 | 2 | — | — | — | 32.5 |
| 160 | 84.0 | 30.1 | 85.6 | 1 | — | — | — | 24.8 |
| 162 | 87.2 | 31.9 | 88.1 | 2 | — | — | — | 27.3 |
| 164 | 83.5 | 29.6 | 84.8 | 1 | — | — | — | 30.1 |
| 166 | 86.8 | 31.8 | 88.2 | 2 | — | — | — | 36.9 |
| Comparative Example | | | | | | | | |
| 21 | 2.1 | 3.2 | 4.6 | 2 | 1.9 | 40.2 | 187 | 3.8 |
| 22 | 1.8 | 1.2 | 2.8 | 1 | 3.8 | 50.8 | 180 | 10.8 |
| 23 | 43.2 | 38.6 | 54.3 | −6 | 40.2 | — | — | 53.6 |

TABLE 16-continued

| | Test Example | | | | | | | |
|---|---|---|---|---|---|---|---|---|
| | 1 (%) | 2 (%) | 3 (%) | 4 (g) | 7 (%) | 9 (%) | 10 (g/cm) | 11 (%) |
| 24 | 42.8 | 36.2 | 52.6 | −4 | 38.5 | — | — | 49.2 |
| Control | — | — | — | 0 | — | — | 175 | — |

The results shown in Table 16 indicate that the external preparation for the treatment of dermatoses according to the third aspect of the present invention are comparable or superior in effect to the conventional, nonsteroidal antiinflammatory agent-containing preparations. Furthermore, the external preparations according to the third aspect of the invention did not show any significant body weight loss due to side effects, unlike the conventional adrenocortical hormone-containing preparations. It was thus proved that the present invention, in its third aspect, provides highly safe external preparations for the treatment of dermatoses, which are widely effective against dermatoses.

EXAMPLES 168 TO 199

Ointments were prepared by supplying white petrolatum (Maruishi Pharmaceutical), bufexamac (Sigma), indomethacin (Sigma), vitamin E acetate (Wako Pure Chemical Industries), squalane (Wako Pure Chemical Industries), squalene (Sigma), N-lauroylsarcosine (Nacalai Tesque), fumaric acid (Nacalai Tesque), cetyl lactate (Van-Dyk) and isopropyl myristate (Nacalai Tesque), in amounts specified below in Tables 17 and 18, to a mortar, and kneading the mortar contents until the components other than white petrolatum were dissolved in the latter.

TABLE 17

| | | Composition (weight %) | | | | | | | | |
|---|---|---|---|---|---|---|---|---|---|---|
| | | White petrolatum | Bufexamac | Indomethacin | Vitamin E | Squalane | Lauroyl-sarcosine | Fumaric acid | Cetyl lactate | Isopropyl myristate |
| Example | 168 | 78.5 | 5 | — | 0.5 | 15 | 1 | — | — | — |
| | 169 | 59.0 | 5 | — | 20 | 15 | 1 | — | — | — |
| | 170 | 29.0 | 5 | — | 50 | 15 | 1 | — | — | — |
| | 171 | 78.5 | 5 | — | 0.5 | 15 | — | 1 | — | — |
| | 172 | 59.0 | 5 | — | 50 | 15 | — | 1 | — | — |
| | 173 | 29.0 | 5 | — | 50 | 15 | — | 1 | — | — |
| | 174 | 78.5 | 5 | — | 0.5 | 15 | — | — | 1 | — |
| | 175 | 59.0 | 5 | — | 20 | 15 | — | — | 1 | — |
| | 176 | 29.0 | 5 | — | 50 | 15 | — | — | 1 | — |
| | 177 | 69.5 | 5 | — | 0.5 | 15 | — | — | — | 10 |
| | 178 | 50.0 | 5 | — | 20 | 15 | — | — | — | 10 |

TABLE 17-continued

| | White petrolatum | Bufexamac | Indomethacin | Vitamin E | Squalane | Lauroyl-sarcosine | Fumaric acid | Cetyl lactate | Isopropyl myristate |
|---|---|---|---|---|---|---|---|---|---|
| 179 | 20.0 | 5 | — | 50 | 15 | — | — | — | 10 |
| 180 | 82.5 | — | 1 | 0.5 | 15 | 1 | — | — | — |
| 181 | 63.0 | — | 1 | 20 | 15 | 1 | — | — | — |
| 182 | 33.0 | — | 1 | 50 | 15 | 1 | — | — | — |
| 183 | 82.5 | — | 1 | 0.5 | 15 | — | 1 | — | — |
| 184 | 63.0 | — | 1 | 20 | 15 | — | 1 | — | — |
| 185 | 33.0 | — | 1 | 50 | 15 | — | 1 | — | — |
| 186 | 82.5 | — | 1 | 0.5 | 15 | — | — | 1 | — |
| 187 | 63.0 | — | 1 | 20 | 15 | — | — | 1 | — |
| 188 | 33.0 | — | 1 | 50 | 15 | — | — | 1 | — |
| 189 | 73.5 | — | 1 | 0.5 | 15 | — | — | — | 10 |
| 190 | 54.0 | — | 1 | 20 | 15 | — | — | — | 10 |
| 191 | 24.0 | — | 1 | 50 | 15 | — | — | — | 10 |

TABLE 18

| Example | White petrolatum | Bufexamac | Indomethacin | Vitamin E | Squalane | Squalene |
|---|---|---|---|---|---|---|
| 192 | 70.0 | 5 | — | 20 | — | 5 |
| 193 | 45.0 | 5 | — | 20 | — | 30 |
| 194 | 55.0 | 5 | — | 20 | 15 | 5 |
| 195 | 15.0 | 5 | — | 20 | 30 | 30 |
| 196 | 74.0 | — | 1 | 20 | — | 5 |
| 197 | 49.0 | — | 1 | 20 | — | 30 |
| 198 | 59.0 | — | 1 | 20 | 15 | 5 |
| 199 | 19.0 | — | 1 | 20 | 30 | 30 |

EXAMPLES 200 TO 213

Liniments were prepared by supplying olive oil (Maruishi Pharmaceutical), bufexamac (Sigma), indomethacin (Sigma), vitamin E acetate (Wako Pure Chemical Industries), squalane (Wako Pure Chemical Industries) and squalene (Sigma), in amounts specified below in Table 19, to a beaker, and stirring the beaker contents until the whole became homogeneous.

TABLE 19

| Example | Olive oil | Bufexamac | Indomethacin | Vitamin E | Squalane | Squalene |
|---|---|---|---|---|---|---|
| 200 | 79.5 | 5 | — | 0.5 | 15 | — |
| 201 | 60.0 | 5 | — | 20 | 15 | — |
| 202 | 30.0 | 5 | — | 50 | 15 | — |
| 203 | 83.5 | — | 1 | 0.5 | 15 | — |
| 204 | 64.0 | — | 1 | 20 | 15 | — |
| 205 | 34.0 | — | 1 | 50 | 15 | — |
| 206 | 70.0 | 5 | — | 20 | — | 5 |
| 207 | 45.0 | 5 | — | 20 | — | 30 |
| 208 | 55.0 | 5 | — | 20 | 15 | 5 |
| 209 | 15.0 | 5 | — | 20 | 30 | 30 |
| 210 | 74.0 | — | 1 | 20 | — | 5 |
| 211 | 49.0 | — | 1 | 20 | — | 30 |
| 212 | 59.0 | — | 1 | 20 | 15 | 5 |
| 213 | 19.0 | — | 1 | 20 | 30 | 30 |

EXAMPLE 214

[Synthesis of acrylic adhesive]

A separable flask equipped with a stirrer and a condenser was charged with 301.1 weight parts of 2-ethylhexyl methacrylate, 34.9 weight parts of 2-ethylhexyl acrylate, 48.3 weight parts of dodecyl methacrylate, 0.0384 weight part of 1,6-hexaneglycol dimethacrylate and 256.0 weight parts of ethyl acetate, and the flask contents were heated to 70° C. with stirring and nitrogen substitution.

A solution of 2.0 weight parts of lauroyl peroxide in 10.0 weight parts of cyclohexane was divided into 10 aliquots. One aliquot was added to the separable flask to thereby initiate the polymerization. Starting at 5 hours after initiation of the polymerization, the remaining 9 aliquots were added one by one at 1-hour intervals. After completion of the addition, the reaction was further carried out for 19 hours. For viscosity adjustment, five 27 weight part portions of ethyl acetate were added one by one at 5-hour intervals after initiation of the reaction.

After completion of the reaction, the reaction mixture was cooled and ethyl acetate was further added to give an adhesive solution with a solid content of 50% by weight.

[Production of tape-form preparation]

The above adhesive solution (120 weight parts), 5 weight parts of bufexamac, 20 weight parts of vitamin E acetate (Wako Pure Chemical Industries) and 15 weight parts of squalane (Wako Pure Chemical Industries) were supplied to a dissolver-type high-speed mixer and homogeneously blended to give a mixed solution.

The thus-obtained mixed solution was applied to a silicone-treated polyethylene terephthalate film (38 μm thick) and then dried at 60° C. for 30 minutes to give a 80-μm-thick adhesive layer.

The above adhesive layer was then transferred onto the ethylene-vinyl acetate copolymer layer of a 34 μm thick polyethylene terephthalate/ethylene-vinyl acetate copolymer laminate film, to give a tape-form preparation.

EXAMPLE 215

A tape-form preparation was obtained in the same manner as in Example 214 except that 15 weight parts of squalene (Sigma) was used in lieu of 15 weight parts of squalane (Wako Pure Chemical Industries).

EXAMPLE 216

A tape-form preparation was obtained in the same manner as in Example 214 except that 15 weight parts of squalane (Wako Pure Chemical Industries) plus 15 weight parts of squalene (Sigma) was used in lieu of 15 weight parts of squalane (Wako Pure Chemical Industries).

EXAMPLE 217

[Synthesis of acrylic adhesive]

The procedure of Example 214 was followed to give an adhesive solution with a solid content of 50% by weight.

[Production of tape-form preparation]

A tape-form preparation was produced in the same manner as in Example 214, using 120 weight parts of the above adhesive solution, 5 weight parts of bufexamac, 10 weight parts of vitamin E acetate (Wako Pure Chemical Industries), 15 weight parts of squalane (Wako Pure Chemical Industries) and 10 weight parts of isopropyl myristate.

EXAMPLE 218

A tape-form preparation was produced in the same manner as in Example 217 except that 15 weight parts of squalene (Sigma) was used in lieu of 15 weight parts of squalane (Wako Pure Chemical Industries).

EXAMPLE 219

A tape-form preparation was produced in the same manner as in Example 217 except that 15 weight parts of squalane (Wako Pure Chemical Industries) plus 15 parts of squalene (Sigma) was used in lieu of 15 weight parts of squalane (Wako Pure Chemical Industries).

EXAMPLES 220 TO 231 AND COMPARATIVE EXAMPLES 25 TO 27

Ointments were prepared by supplying Plastibase (Taisho Pharmaceutical), diphenhydramine (Kongo Chemical), vitamin E acetate (Wako Pure Chemical Industries), squalane (Wako Pure Chemical Industries), squalene (Sigma), isopropyl myristate (Nacalai Tesque), dexamethasone (Wako Pure Chemical Industries) and prednisolone (Wako Pure Chemical Industries), in amounts specified below in Table 20, to a mortar, and kneading the mortar contents until the components other than Plastibase were dissolved in the latter.

In Table 20 as well as in Table 22 (to be given later herein), IPM stands for isopropyl myristate, and DH for diphenhydramine.

The thus-obtained ointments were tested as in Test Examples 1, 4, 7 and 9 to 11. In Test Examples 1 to 4, 7, 10 and 11, each ointment was tested using 5 rats and the results expressed in terms of mean value. In Test Example 9, each ointment was tested using 5 guinea pigs and the results were expressed in terms of mean value. The results thus obtained are shown in Table 21.

TABLE 21

| | Test Example | | | | | | | |
|---|---|---|---|---|---|---|---|---|
| | 1 (%) | 2 (%) | 3 (%) | 4 (g) | 7 (%) | 9 (%) | 10 (g/cm) | 11 (%) |
| Example | | | | | | | | |
| 220 | 20.1 | 53.3 | 23.9 | 2 | — | — | — | 10.1 |
| 221 | 81.2 | 74.8 | 84.1 | 1 | 18.7 | 29.6 | 228 | 24.7 |
| 222 | 84.6 | 75.2 | 82.6 | 3 | — | — | — | 28.1 |
| 222 | 87.3 | 78.8 | 87.7 | 0 | — | — | — | 31.8 |
| 224 | 88.8 | 80.3 | 89.9 | 1 | — | — | — | 32.7 |
| 225 | 25.7 | 64.6 | 30.3 | 2 | — | — | — | 14.4 |
| 226 | 85.5 | 77.5 | 88.8 | 1 | 30.1 | 35.4 | 240 | 29.6 |
| 227 | 87.8 | 77.8 | 88.9 | 1 | — | — | — | 30.3 |
| 228 | 82.9 | 81.4 | 84.8 | 1 | — | — | — | 25.8 |
| 229 | 88.3 | 85.5 | 87.2 | 2 | — | — | — | 30.2 |
| 230 | 89.1 | 86.3 | 88.1 | 1 | — | — | — | 31.1 |
| 231 | 90.1 | 89.3 | 89.9 | 2 | — | — | — | 33.0 |
| Comparative Example | | | | | | | | |
| 25 | 3.9 | 51.3 | 4.1 | 2 | 6.2 | 5.7 | 182 | 2.6 |
| 26 | 43.2 | 38.6 | 54.3 | −6 | 40.2 | — | — | 53.6 |
| 27 | 42.8 | 36.2 | 52.6 | −4 | 38.5 | — | — | 49.2 |
| Control | — | — | — | 0 | — | — | 175 | — |

The results shown in Table 21 indicate that the external preparation for the treatment of dermatoses according to the fourth aspect of the present invention are comparable or superior in effect to the conventional, antihistaminic agent-containing preparations. Furthermore, the external preparations according to the fourth aspect of the invention did not show any significant body weight loss due to side effects, unlike the conventional adrenocortical hormone-containing preparations. It was thus proved that the present invention, in its fourth aspect, provides highly safe external preparations for the treatment of dermatoses, which are widely effective against dermatoses.

TABLE 20

| | | Composition (weight %) | | | | | | | |
|---|---|---|---|---|---|---|---|---|---|
| | | Plastibase | DH | Vitamin E | Squalane | Squalene | IPM | Dexamethasone | Prednisolone |
| Example | 220 | 83.5 | 1 | 0.5 | 15 | — | — | — | — |
| | 221 | 64 | 1 | 20 | 15 | — | — | — | — |
| | 222 | 49 | 1 | 20 | 30 | — | — | — | — |
| | 223 | 34 | 1 | 50 | 15 | — | — | — | — |
| | 224 | 19 | 1 | 50 | 30 | — | — | — | — |
| | 225 | 73.5 | 1 | 0.5 | 15 | — | 10 | — | — |
| | 226 | 54 | 1 | 20 | 15 | — | 10 | — | — |
| | 227 | 39 | 1 | 20 | 30 | — | 10 | — | — |
| | 228 | 73 | 2 | 20 | — | 5 | — | — | — |
| | 229 | 48 | 2 | 20 | — | 30 | — | — | — |
| | 230 | 58 | 2 | 20 | 15 | 5 | — | — | — |
| | 231 | 18 | 2 | 20 | 30 | 30 | — | — | — |
| Comparative Example | 25 | 99 | 1 | — | — | — | — | — | — |
| | 26 | 99.9 | — | — | — | — | — | 0.1 | — |
| | 27 | 99.5 | — | — | — | — | — | — | 0.5 |

EXAMPLES 232 TO 247

Ointments were prepared by supplying white petrolatum (Maruishi Pharmaceutical), diphenhydramine (Kongo Chemcial), vitamin E acetate (Wako Pure Chemical Industries), squalane (Wako Pure Chemical Industries), squalene (Sigma), N-lauroylsarcosine (Nacalai Tesque), fumaric acid (Nacalai Tesque), cetyl lactate (Van Dyk) and isopropyl myristate (Nacalai Tesque), in amounts specified below in Table 22, to a mortar, and kneading the mortar contents until the components other than white petrolatum were dissolved in the latter.

In Table 22, LS stands for N-lauroylsarcosine.

TABLE 22

| | | \multicolumn{8}{c}{Composition (weight %)} | | | | | | | |
|---|---|---|---|---|---|---|---|---|---|
| | | White petrolatum | DH | Vitamin E | Squalane | Squalene | LS | Fumaric acid | Cetyl lactate | IPM |
| Example | 232 | 82.5 | 1 | 0.5 | 15 | — | 1 | — | — | — |
| | 233 | 63.0 | 1 | 20 | 15 | — | 1 | — | — | — |
| | 224 | 33.0 | 1 | 50 | 15 | — | 1 | — | — | — |
| | 235 | 82.5 | 1 | 0.5 | 15 | — | — | 1 | — | — |
| | 236 | 63.0 | 1 | 20 | 15 | — | — | 1 | — | — |
| | 237 | 33.0 | 1 | 50 | 15 | — | — | 1 | — | — |
| | 238 | 82.5 | 1 | 0.5 | 15 | — | — | — | 1 | — |
| | 239 | 63.0 | 1 | 20 | 15 | — | — | — | 1 | — |
| | 240 | 33.0 | 1 | 50 | 15 | — | — | — | 1 | — |
| | 241 | 73.5 | 1 | 0.5 | 15 | — | — | — | — | 10 |
| | 242 | 54.0 | 1 | 20 | 15 | — | — | — | — | 10 |
| | 243 | 24.0 | 1 | 50 | 15 | — | — | — | — | 10 |
| | 244 | 73.0 | 2 | 20 | — | 5 | — | — | — | — |
| | 245 | 48.0 | 2 | 20 | — | 30 | — | — | — | — |
| | 246 | 58.0 | 2 | 20 | 15 | 5 | — | — | — | — |
| | 247 | 18.0 | 2 | 20 | 30 | 30 | — | — | — | — |

EXAMPLES 248 TO 254

Liniments were prepared by feeding olive oil (Maruishi Pharmaceutical), diphenhydramine (Kongo Chemical), vitamin E acetate (Wako Chemical Industries), squalane (Wako Pure Chemical Industries) and squalene (Sigma), in amounts specified below in Table 23, to a beaker, and stirring the beaker contents until the whole became homogeneous.

TABLE 23

| | | \multicolumn{5}{c}{Composition (weight %)} | | | | |
|---|---|---|---|---|---|---|
| | | Olive oil | Diphen-hydra-mine | Vita-min E | Squa-lane | Squa-lene |
| Example | 248 | 83.5 | 1 | 0.5 | 15 | — |
| | 249 | 64.0 | 1 | 20 | 15 | — |
| | 250 | 34.0 | 1 | 50 | 15 | — |
| | 251 | 73.0 | 2 | 20 | — | 5 |
| | 252 | 48.0 | 2 | 20 | — | 30 |
| | 253 | 58.0 | 2 | 20 | 15 | 5 |
| | 254 | 18.0 | 2 | 20 | 30 | 30 |

EXAMPLE 255

[Synthesis of acrylic adhesive]

A separable flask equipped with a stirrer and a condenser was charged with 301.1 weight parts of 2-ethylhexyl methacrylate, 34.9 weight parts of 2-ethylhexyl acrylate, 48.3 weight parts of dodecyl methacrylate, 0.0384 weight part of 1,6-hexaneglycol dimethacrylate and 256.0 weight parts of ethyl acetate, and the flask contents were heated to 70° C. with stirring and nitrogen substitution.

A solution of 2.0 weight parts of lauroyl peroxide in 10.0 weight parts of cyclohexane was divided into 10 aliquots. One aliquot was added to the separable flask to thereby initiate the polymerization. Starting at 5 hours after initiation of the polymerization, the remaining 9 aliquots were added portion by portion at 1-hour intervals. After completion of the addition, the reaction was further carried out for 19 hours. For viscosity adjustment, five 27 weight part portions of ethyl acetate were added portion by portion at 5-hour intervals after initiation of the reaction.

After completion of the reaction, the reaction mixture was cooled and ethyl acetate was further added to give an adhesive solution with a solid content of 50% by weight.

[Production of tape-form preparation]

The above adhesive solution (128 weight parts), 1 weight parts of diphenhydramine, 20 weight parts of vitamin E acetate (Wako Pure Chemical Industries) and 15 weight parts of squalane (Wako Pure Chemical Industries) were fed to a dissolver-type high-speed mixer and homogeneously blended to give a mixed solution.

The thus-obtained mixed solution was applied to a silicone-treated polyethylene terephthalate film (38 $\mu$m thick) and then dried at 60° C. for 30 minutes to give a 80-$\mu$m-thick adhesive layer.

The above adhesive layer was then transferred onto the ethylene-vinyl acetate copolymer layer of a 34 $\mu$m thick polyethylene terephthalate/ethylene-vinyl acetate copolymer laminate film, to give a tape-form preparation.

EXAMPLE 256

A tape-form preparation was obtained in the same manner as in Example 255 except that 15 weight parts of squalene (Sigma) was used in lieu of 15 weight parts of squalane (Wako Pure Chemical Industries).

EXAMPLE 257

A tape-form preparation was obtained in the same manner as in Example 255 except that 15 weight parts of squalane (Wako Pure Chemical Industries) plus 15 weight parts of squalene (Sigma) was used in lieu of 15 weight parts of squalane (Wako Pure Chemical Industries).

EXAMPLE 258

[Synthesis of acrylic adhesive]

The procedure of Example 255 was followed to give an adhesive solution with a solid content of 50%.

[Production of tape-form preparation]

A tape-form preparation was obtained in the same manner as in Example 255, using 128 weight parts of the above adhesive solution, 1 weight part of diphenhydramine, 10 weight parts of vitamin E acetate (Wako Pure Chemical Industries), 15 weight parts of squalane (Wako Pure Chemical Industries) and 10 weight parts of isopropyl myristate.

EXAMPLE 259

A tape-form preparation was obtained in the same manner as in Example 258 except that 15 weight parts of squalene (Sigma) was used in lieu of 15 weight parts of squalane (Wako Pure Chemical Industries).

EXAMPLE 260

A tape-form preparation was obtained in the same manner as in Example 258 except that 15 weight parts of squalane (Wako Pure Chemical Industries) plus 15 parts of squalene (Sigma) was used in lieu of 15 weight parts of squalane (Wako Pure Chemical Industries).

EXAMPLES 261 TO 278 AND COMPARATIVE EXAMPLES 28 TO 41

Ointments were prepared by feeding Plastibase (Taisho Pharmaceutical), vitamin E acetate (Wako Pure Chemical Industries), squalene (Sigma), squalane (Wako Pure Chemical Industries), isopropyl myristate (Nacalai Tesque), dexamethasone (Wako Pure Chemical Industries) and prednisolone (Wako Pure Chemical Industries), in amounts (parts by weight) specified below in Tables 24 and 25, to a mortar, and kneading the mortar contents until the components other than Plastibase were dissolved in the latter.

In Tables 24 and 25 as well as in Tables 30 and 32 (to be given later herein), VE stands for vitamin E acetate, SQE for squalene, SQA for squalane, IPM for isopropyl myristate, Dx for dexamethasone, and Pr for prednisolone.

TABLE 24

| | | Composition (weight %) | | | | |
|---|---|---|---|---|---|---|
| | | Plastibase | VE | SQE | SQA | IPM |
| Example | 261 | 81.5 | 2 | 1.5 | 15 | — |
| | 262 | 78.5 | 5 | 1.5 | 15 | — |
| | 263 | 87.0 | 10 | 1.5 | 1.5 | — |
| | 264 | 73.5 | 10 | 1.5 | 15 | — |
| | 265 | 58.5 | 10 | 1.5 | 30 | — |
| | 266 | 43.5 | 10 | 1.5 | 45 | — |
| | 267 | 60.0 | 10 | 15 | 15 | — |
| | 268 | 45.0 | 10 | 15 | 30 | — |
| | 269 | 30.0 | 10 | 15 | 45 | — |
| | 270 | 45.0 | 10 | 30 | 15 | — |
| | 271 | 63.5 | 20 | 1.5 | 15 | — |
| | 272 | 50.0 | 20 | 15 | 15 | — |
| | 273 | 35.0 | 20 | 15 | 30 | — |
| | 274 | 43.5 | 40 | 1.5 | 15 | — |
| | 275 | 23.5 | 60 | 1.5 | 15 | — |
| | 276 | 71.5 | 2 | 1.5 | 15 | 10 |
| | 277 | 63.5 | 10 | 1.5 | 15 | 10 |
| | 278 | 53.5 | 20 | 1.5 | 15 | 10 |

TABLE 25

| | | Composition (weight %) | | | | | |
|---|---|---|---|---|---|---|---|
| | | Plastibase | VE | SQE | IPM | Dx | Pr |
| Comparative Example | 28 | 96.5 | 2 | 1.5 | — | — | — |
| | 29 | 93.5 | 5 | 1.5 | — | — | — |
| | 30 | 88.5 | 10 | 1.5 | — | — | — |
| | 31 | 75.0 | 10 | 15 | — | — | — |
| | 32 | 60.0 | 10 | 30 | — | — | — |
| | 33 | 78.5 | 20 | 1.5 | — | — | — |
| | 34 | 65.0 | 20 | 15 | — | — | — |
| | 35 | 58.5 | 40 | 1.5 | — | — | — |
| | 36 | 38.5 | 60 | 1.5 | — | — | — |
| | 37 | 86.5 | 2 | 1.5 | 10 | — | — |
| | 38 | 78.5 | 10 | 1.5 | 10 | — | — |
| | 39 | 68.5 | 20 | 1.5 | 10 | — | — |
| | 40 | 99.9 | — | — | — | 0.1 | — |
| | 41 | 99.5 | — | — | — | — | 0.5 |

The thus-obtained ointments were tested as in Test Examples 1 to 5, 7 and 11 and further tested according to the methods mentioned below in Test Examples 12 to 14. In Test Examples 1 to 4, 7, 11, 12 and 14, each ointment was tested using 5 rats and the results were expressed in terms of mean value. In Test Example 13, each ointment was tested using 5 guinea pigs and the results were expressed in terms of mean value. The results thus obtained are shown in Tables 26 to 29.

TEST EXAMPLE 12

Effect on Type II Allergic Reaction (1) Preparation of Rabbit Anti-rat Serum

Rabbit anti-rat serum was prepared by the method of Eda et al. (Folia Pharmacologica Japonica; 66, 237, 1970).

Thus, serum was collected from male Wistar rats weighing 150 to 200 g. An equivolume mixture (emulsion) of this rat serum and Freund's complete adjuvant (Difco) was used as an antigen preparation and 0.5 ml thereof was injected into the right and left gluteal muscles of each male rabbit (New Zealand white strain) four times at one-week intervals. Seven days after the last injection, blood was collected from the carotid artery and serum was separated and recovered. Thus, rabbit anti-rat serum was obtained.

(2) Effect on Anti-rat Serum-induced Intradermal Reaction

The ointments were examined for effect on anti-rat serum-induced intracutaneous reaction by the method of Kuriyama et al. (Folia Pharmacologica Japonica; 95, 83, 1990).

The above rabbit anti-rat serum was 4-fold diluted with physiological saline and 0.1 ml of the dilution was intradermally injected into the back of each male Wistar rat weighing about 200 g. Then, 0.1 g of each of the ointments obtained in the above-mentioned examples and comparative examples was applied to the rat skin at the site of application of the anti-rat serum in the same manner as in Test Example 1.

Further, 2 hours thereafter, 0.5% Evans' blue solution in physiological saline was intravenously administered at a dose of 2.5 ml/kg.

The dye that had leaked out at the site of the thus-induced reaction was extracted and assayed by the method of Harada et al. (Journal of Pharmaceutics Pharmacology; 23, 218, 1971).

Thus, 30 minutes after Evans' blue administration, the animals were sacrificed. The skin containing the dye that had leaked out was excised from the reaction area, minced and immersed in a mixed solution composed of 0.3% aqueous solution of sodium sulfate and acetone (3:7, v/v) for at least 48 hours for effecting extraction of the dye that had leaked out. The dye thus extracted was then assayed by absorbance at 620 nm.

As a control, the ointment base (Plastibase) alone was applied in lieu of the test preparation. Thereafter, the same procedure was followed and the dye extracted was assayed by absorbance.

From the results of determination of the amount (O) of the dye extracted from the site of application of the control and of the amount (P) of the dye extracted from the site of application of each test preparation, the dye-leakage inhibition percentage was calculated as follows:

Dye-leakage inhibition (%)=[(O−P)/O]×100

The results thus obtained are shown in Tables 28 and 29.

TEST EXAMPLE 13

Effect on Solar Dermatitis (ultraviolet erythema)

The ointments were examined for effect on ultraviolet-induced erythema by the method of Tsuji et al. (Oyo Yakuri; 23, 567, 1982). Thus, the back of guinea pigs weighing 250 to 300 g was clipped of hairs. The skin of the back was covered with a light-shielding cloth having three round holes with a diameter of 7 mm and ultraviolet irradiation was carried out from a distance of 20 cm for 30 seconds using a 1,000 watt ultraviolet lamp (Toshiba). Immediately thereafter, 0.1 g of each of the ointments obtained in the above-mentioned examples and comparative examples was applied as the test preparation to the site of ultraviolet-induced erythema in the same manner as in Test Example 1.

After 24 hours, the skin reactions were scored according to the criteria shown below and the sum of scores for the three sites was used for evaluating each test preparation.

As a control, the ointment base (Plastibase) alone was applied in the same manner in lieu of the test preparation and thereafter the skin reactions were evaluated by the same procedure.
Evaluation Criteria
0: No change
1: Slight erythema
2: Medium erythema
3: Marked erythema
4: Marked erythema and edema From the erythema score (M) for the control and the erythema score (N) for the test preparation application sites, the ultraviolet-induced erythema healing percentage was calculated as follows:

UV-induced erythema healing (%)=[(M−N)/M]×100

The results thus obtained are shown in Table 28 and 29.

TEST EXAMPLE 14

Effect on Wound Healing

The ointments were evaluated for effect on wound healing by the method of Sakyo et al. (Oyo Yakuri; 43, 121, 1992). The back of 5-week-old Wistar rats was shaved of hairs and using a surgical knife, a 30 mm-long incision was made along the median line under ether anesthesia. Immediately after incision, the wound was sutured in 3 equispaced positions.

Then, 0.2 g samples from the ointments obtained in the above examples and comparative examples were respectively spread on gauze (3-ply), 2.5 cm×5 cm, and applied against the wounded area and an occlusive dressing using a stretchable bandage was applied for fixation. The ointment-coated gauze was exchanged once/daily.

The suture was removed 3 days after commencement of the experiment. On day 8, the skin covering the whole wounded area was excised from each rat and 1 cm-wide skin strips parallel to the wound line (2 strips/rat) were prepared. Both ends of each strip were fixed to an NRM-3002D-L rheometer (FUDOH) and the tension force (g/cm) required for cutting the strip at the wound site was measured. The mean measured value for two strips was taken as the tension value for one sample.

As a control, the ointment base (Plastibase) alone was applied in the same manner in lieu of the test preparation and thereafter tension measurements were carried out following the same procedure.

From the tensile strength (Q) of the healed wound in the control group and the tensile strength (R) of the healed wound for the test preparation application sites, the wound healing percentage was calculated as follows:

Wound healing (%)=[(Q−R)/Q]×100

The results are shown in Table 28 and 29.

TABLE 26

|  |  | Test Example | | | |
|---|---|---|---|---|---|
|  |  | 1 (%) | 2 (%) | 3 (%) | 4 (g) |
| Example | 261 | 25.0 | 20.9 | 31.1 | 0 |
|  | 262 | 30.9 | 24.1 | 37.0 | 1 |
|  | 263 | 30.3 | 23.9 | 36.6 | 1 |
|  | 264 | 40.5 | 34.9 | 43.7 | 2 |
|  | 265 | 45.8 | 41.9 | 49.7 | 2 |
|  | 266 | 56.0 | 48.5 | 59.1 | 2 |
|  | 267 | 54.7 | 47.4 | 59.4 | 2 |
|  | 268 | 61.3 | 56.7 | 67.3 | 2 |
|  | 269 | 64.1 | 60.3 | 74.9 | 3 |
|  | 270 | 77.0 | 72.4 | 89.9 | 3 |
|  | 271 | 52.2 | 44.6 | 55.3 | 2 |
|  | 272 | 70.1 | 59.9 | 74.3 | 2 |
|  | 273 | 80.3 | 72.1 | 84.6 | 3 |
|  | 274 | 67.3 | 58.9 | 67.6 | 2 |
|  | 275 | 71.7 | 62.4 | 70.7 | 3 |
|  | 276 | 36.2 | 27.1 | 45.6 | 2 |
|  | 277 | 52.9 | 40.1 | 57.0 | 2 |
|  | 278 | 73.2 | 67.2 | 81.5 | 2 |

TABLE 27

|  |  | Test Example | | | |
|---|---|---|---|---|---|
|  |  | 1 (%) | 2 (%) | 3 (%) | 4 (g) |
| Comparative | 28 | 19.2 | 14.9 | 24.3 | −1 |
| Example | 29 | 23.8 | 17.2 | 28.9 | −1 |
|  | 30 | 27.2 | 21.3 | 30.1 | 0 |
|  | 31 | 31.2 | 25.1 | 34.4 | 1 |
|  | 32 | 35.2 | 29.7 | 38.9 | 1 |
|  | 33 | 38.6 | 33.0 | 41.0 | 1 |
|  | 34 | 45.3 | 38.4 | 46.7 | 0 |
|  | 35 | 49.9 | 43.6 | 50.1 | 2 |
|  | 36 | 53.1 | 46.2 | 52.4 | 2 |
|  | 37 | 26.8 | 20.1 | 33.8 | 0 |
|  | 38 | 39.2 | 29.7 | 42.2 | 1 |
|  | 39 | 53.1 | 45.2 | 58.1 | 2 |
|  | 40 | 51.4 | 43.2 | 54.8 | −13 |
|  | 41 | 52.0 | 42.1 | 54.9 | −12 |
| Control |  | — | — | — | 0 |

TABLE 28

| | | Test Examples | | | | |
|---|---|---|---|---|---|---|
| | | 5 | 7 (%) | 11 (%) | 12 (%) | 13 (%) | 14 (%) |
| Example | 261 | 2 | — | 15.7 | — | 5.3 | — |
| | 262 | 2 | — | 21.1 | — | — | — |
| | 263 | 2 | — | 20.7 | — | — | — |
| | 264 | 2 | 24.2 | 26.2 | 24.1 | 10.1 | 19.1 |
| | 265 | 2 | — | 30.9 | — | — | — |
| | 266 | 1 | — | 36.1 | — | — | — |
| | 267 | 2 | 33.8 | 35.3 | 33.9 | 16.1 | 27.1 |
| | 268 | 1 | — | 41.9 | — | — | — |
| | 269 | 0 | — | 45.1 | — | — | — |
| | 270 | 1 | — | 54.1 | — | 21.3 | — |
| | 271 | 2 | 32.9 | 35.3 | 33.1 | 15.6 | 26.5 |
| | 272 | 2 | — | 44.2 | — | 19.8 | — |
| | 273 | 0 | — | 53.1 | — | — | — |
| | 274 | 1 | — | 46.6 | — | — | — |
| | 275 | 0 | — | 49.8 | — | — | — |
| | 276 | 2 | — | 23.1 | — | 10.1 | — |
| | 277 | 2 | 33.8 | 33.9 | 33.5 | 16.5 | 28.1 |
| | 278 | 2 | 70.3 | 56.2 | 71.2 | 22.4 | 64.3 |

TABLE 29

| | | Test Examples | | | | |
|---|---|---|---|---|---|---|
| | | 5 | 7 (%) | 11 (%) | 12 (%) | 13 (%) | 14 (%) |
| Comparative Example | 28 | 2 | — | 12.1 | — | 2.1 | — |
| | 29 | 2 | — | 16.2 | — | — | — |
| | 30 | 2 | 13.2 | 17.6 | 14.1 | 5.9 | 10.0 |
| | 31 | 2 | — | 20.1 | — | — | — |
| | 32 | 2 | — | 23.9 | — | — | — |
| | 33 | 2 | 21.8 | 26.2 | 22.1 | 8.2 | 16.8 |
| | 34 | 2 | — | 31.2 | — | — | — |
| | 35 | 2 | — | 34.5 | — | — | — |
| | 36 | 0 | — | 36.9 | — | — | — |
| | 37 | 2 | — | 17.1 | — | 5.4 | — |
| | 38 | 2 | 22.5 | 25.1 | 23.1 | 8.6 | 17.2 |
| | 39 | 2 | 33.0 | 41.2 | 34.1 | 11.3 | 28.1 |
| | 40 | 2 | — | 40.3 | — | 8.2 | — |
| | 41 | 2 | — | 39.7 | — | 5.4 | — |
| Control | | — | — | — | — | — | — |

EXAMPLES 279 TO 288 AND COMPARATIVE EXAMPLES 42 TO 56

Ointments were prepared by feeding white petrolatum (Maruishi Pharmaceutical), vitamin E acetate (Wako Pure Chemical Industries), squalene (Sigma), squalane (Wako Pure Chemical Industries), N-lauroylsarcosine (Nacalai Tesque), fumaric acid (Nacalai Tesque), cetyl lactate (Van-Dyk) and isopropyl myristate (Nacalai Tesque), in amounts (parts by weight) specified below in Table 30, to a mortar, and kneading the mortar contents until the components other than white petrolatum were dissolved in the latter.

In Table 30, LS stands for N-lauroylsarcosine.

TABLE 30

| | | Composition (weight %) | | | | | | | |
|---|---|---|---|---|---|---|---|---|---|
| | | White petrolatum | VE | SQE | SQA | LS | Fumaric acid | Cetyl lactate | IPM |
| Example | 279 | 62.5 | 20 | 1.5 | 15 | 1 | — | — | — |
| | 280 | 49 | 20 | 15 | 15 | 1 | — | — | — |
| | 281 | 62.5 | 20 | 1.5 | 15 | — | 1 | — | — |
| | 282 | 49 | 20 | 15 | 15 | — | 1 | — | — |
| | 283 | 62.5 | 20 | 1.5 | 15 | — | — | 1 | — |
| | 284 | 49 | 20 | 15 | 15 | — | — | 1 | — |
| | 285 | 53.5 | 20 | 1.5 | 15 | — | — | — | 10 |
| | 286 | 40 | 20 | 15 | 15 | — | — | — | 10 |
| | 287 | 63.5 | 20 | 1.5 | 15 | — | — | — | — |
| | 288 | 50 | 20 | 15 | 15 | — | — | — | — |
| Comparative Example | 42 | 77.5 | 20 | 1.5 | — | 1 | — | — | — |
| | 43 | 64 | 20 | 15 | — | 1 | — | — | — |
| | 44 | 44 | 40 | 15 | — | 1 | — | — | — |
| | 45 | 77.5 | 20 | 1.5 | — | — | 1 | — | — |
| | 46 | 64 | 20 | 15 | — | — | 1 | — | — |
| | 47 | 44 | 40 | 15 | — | — | 1 | — | — |
| | 48 | 77.5 | 20 | 1.5 | — | — | — | 1 | — |
| | 49 | 64 | 20 | 15 | — | — | — | 1 | — |
| | 50 | 44 | 40 | 15 | — | — | — | 1 | — |
| | 51 | 68.5 | 20 | 1.5 | — | — | — | — | 10 |
| | 52 | 55 | 20 | 15 | — | — | — | — | 10 |
| | 53 | 35 | 40 | 15 | — | — | — | — | 10 |
| | 54 | 78.5 | 20 | 1.5 | — | — | — | — | — |
| | 55 | 65 | 20 | 15 | — | — | — | — | — |
| | 56 | 45 | 40 | 15 | — | — | — | — | — |

The thus-obtained ointments were tested as in Test Examples 1 to 3 and 11. The results obtained are shown in Table 31.

TABLE 31

| | | Test Example | | | |
|---|---|---|---|---|---|
| | | 1 (%) | 2 (%) | 3 (%) | 11 (%) |
| Example | 279 | 72.1 | 66.4 | 78.9 | 56.1 |
| | 280 | — | — | — | 61.3 |
| | 281 | 71.2 | 66.0 | 78.5 | 55.9 |
| | 282 | — | — | — | 60.3 |
| | 283 | 73.1 | 66.8 | 79.8 | 56.3 |
| | 284 | — | — | — | 61.9 |
| | 285 | 72.2 | 66.9 | 80.7 | 56.1 |
| | 286 | — | — | — | 62.3 |
| | 287 | 51.9 | 44.4 | 55.3 | 34.8 |
| | 288 | 69.5 | 57.8 | 71.3 | 42.8 |
| Comparative Example | 42 | 51.0 | 47.8 | 56.8 | 38.9 |
| | 43 | — | — | — | 41.2 |
| | 44 | — | — | — | 47.3 |
| | 45 | 52.1 | 45.8 | 54.6 | 39.1 |
| | 46 | — | — | — | 41.5 |
| | 47 | — | — | — | 47.3 |
| | 48 | 52.8 | 45.2 | 57.6 | 39.8 |
| | 49 | — | — | — | 42.1 |
| | 50 | — | — | — | 47.8 |
| | 51 | 52.8 | 45.0 | 57.8 | 40.7 |
| | 52 | — | — | — | 43.2 |
| | 53 | — | — | — | 48.6 |
| | 54 | 38.4 | 32.6 | 40.6 | 25.8 |
| | 55 | 45.2 | 38.1 | 46.5 | 30.8 |
| | 56 | — | — | — | 36.8 |

EXAMPLES 289 TO 292 AND COMPARATIVE EXAMPLES 57 AND 58

Liniments were prepared by feeding olive oil (Maruishi Pharmaceutical), vitamin E acetate (Wako Pure Chemical Industries), squalene (Sigma) and squalane (Wako Pure Chemical Industries), in amounts (parts by weight) specified below in Table 32, to a beaker, and stirring the beaker contents until the whole became homogeneous.

The thus-obtained liniments were tested as in Test Examples 1 to 3 and 11. The results obtained are shown in Table 32.

TABLE 32

| | External preparation composition (weight %) | | | | Test Example | | | |
|---|---|---|---|---|---|---|---|---|
| | Olive oil | VE | SQE | SQA | 1 (%) | 2 (%) | 3 (%) | 11 (%) |
| Example | | | | | | | | |
| 289 | 73.5 | 10 | 1.5 | 15 | — | — | — | 27.5 |
| 290 | 60 | 10 | 15 | 15 | — | — | — | 36.2 |
| 291 | 63.5 | 20 | 1.5 | 15 | 52.3 | 45.9 | 55.6 | 35.1 |
| 292 | 50 | 20 | 15 | 15 | 70.1 | 58.1 | 71.4 | 43.1 |
| Comparative Example | | | | | | | | |
| 57 | 75 | 10 | 15 | — | — | — | — | 21.3 |
| 58 | 65 | 20 | 15 | — | 46.3 | 39.6 | 47.8 | 33.1 |

The results shown in Tables 26 to 29, 31 and 32 indicate that the external preparation for the treatment of dermatoses according to the fifth aspect of the present invention are comparable or superior in effect to the vitamin E-squalene mixtures and the vitamin E-squalene mixtures supplemented with a transdermal absorption enhancer. Furthermore, when the external preparations according to the fifth aspect of the present invention were used, any significant body weight loss due to side effects was observed, unlike the case of the adrenocortical hormone-containing external preparations. It was thus shown that the present invention, in its fifth aspect, provides highly safe external preparations for the treatment of dermatoses, which are widely effective against dermatoses.

EXAMPLE 293

[Synthesis of acrylic adhesive]

A separable flask equipped with a stirrer and a condenser was charged with 301.1 weight parts of 2-ethylhexyl methacrylate, 34.9 weight parts of 2-ethylhexyl acrylate, 48.3 weight parts of dodecyl methacrylate, 0.0384 weight part of 1,6-hexaneglycol dimethacrylate and 256.0 weight parts of ethyl acetate, and the flask contents were heated to 70° C. with stirring and nitrogen substitution.

A solution of 2.0 weight parts of lauroyl peroxide in 100.0 weight parts of cyclohexane was divided into 10 aliquots. One aliquot was added to the separable flask to thereby initiate the polymerization. Starting at 5 hours after initiation of the polymerization, the remaining 9 aliquots were added one by one at 1-hour intervals. After completion of the addition, the reaction was further carried out for 19 hours. For viscosity adjustment, five 27 weight part portions of ethyl acetate were added portion by portion at 5-hour intervals after initiation of the reaction.

After completion of the reaction, the reaction mixture was cooled and ethyl acetate was further added to give an adhesive solution with a solid content of 50% by weight.

[Production of tape-form preparation]

The above adhesive solution (100 weight parts), 20 weight parts of vitamin E acetate (Wako Pure Chemical Industries), 15 weight parts of squalene (Sigma) and 15 weight parts of squalane (Wako Pure Chemical Industries) were fed to a dissolver-type high-speed mixer and homogeneously blended to give a mixed solution.

The thus-obtained mixed solution was applied to a silicone-treated polyethylene terephthalate film (38 μm thick) and then dried at 60° C. for 30 minutes to give a 80-μm-thick adhesive layer.

The above adhesive layer was then transferred onto the ethylene-vinyl acetate copolymer layer of a 34 μm thick polyethylene terephthalate/ethylene-vinyl acetate copolymer laminate film, to give a tape-form preparation.

EXAMPLE 294

[Synthesis of acrylic adhesive]

The procedure of Example 293 was followed to give an adhesive solution with a solid content of 50% by weight.

[Production of tape-form preparation]

A tape-form preparation was obtained in the same manner as in Example 293, using 127 weight parts of the above adhesive solution, 10 weight parts of vitamin E acetate (Wako Pure Chemical Industries), 1.5 weight parts of squalene (Sigma), 15 weight parts of squalane (Wako Pure Chemical Industries) and 10 weight parts of isopropyl myristate.

INDUSTRIAL APPLICABILITY

Being constituted as detailedly described hereinabove, the external preparation for the treatment of dermatoses according to the first aspect of the present invention shows high therapeutic effects against dermatoses with reduced side effects as compared with external preparations whose main component is an adrenocortical hormone. Therefore, external preparations useful in the treatment of various dermatoses can be obtained.

The external preparation for the treatment of dermatoses according to the second aspect of the present invention contains vitamin E and squalane in addition to an adrenocortical hormone and therefore shows a higher therapeutic effect against intractable dermatoses as compared with the case where the adrenocortical hormone is used alone. The addition of vitamin E and squalane within respective specific concentration ranges is more effective and makes it possible to obtain high therapeutic effects on dermatoses with low adrenocortical hormone concentrations. Therefore, external preparations for the treatment of dermatoses which can be provided show high curative effects with reduction in side effects due to adrenocortical hormones. Furthermore, when said preparation further contains a specific transdermal absorption enhancer, the active ingredients can readily be adsorbed into the skin and high therapeutic effects can be produced against intractable dermatoses.

The external preparation for the treatment of dermatoses according to the third aspect of the present invention, which contains a nonsteroidal antiinflammatory agent, vitamin E and squalane and/or squalene, produces high therapeutic effects on intractable dermatoses with reduced side effects as compared with external preparations containing an adrenocortical hormone as a main active ingredient. Therefore, external preparations useful in various dermatoses can be obtained. In particular, when the nonsteroidal antiinflammatory agent, vitamin E and squalane and/or squalene are used within respective specific concentration ranges, external preparations useful in various dermatoses can be obtained more efficiently. Furthermore, when said preparation further contains a specific transdermal absorption enhancer, the active ingredients can readily be adsorbed into the skin and high therapeutic effects can be produced even against intractable dermatoses, with reduced side effects as compared with external preparations containing an adrenocortical hormone as a main active ingredient. Thus, external preparations useful in the treatment of various dermatoses can be obtained.

The external preparation for the treatment of dermatoses according to the fourth aspect of the present invention, which contains an antihistaminic agent, vitamin E and squalane and/or squalene, produces high therapeutic effects even on intractable dermatoses with reduced side effects as compared with external preparations containing an adrenocortical hormone as a main active ingredient. Therefore, external preparations useful in various dermatoses can be obtained. In particular, when the antihistaminic agent, vitamin E and squalane and/or squalene are used within respective specific concentration ranges, external preparations useful in various dermatoses can be obtained more efficiently. Furthermore, when said preparation further contains a specific transdermal absorption enhancer, the active ingredients can readily be adsorbed into the skin and high therapeutic effects can be produced even against intractable dermatoses, with reduced side effects as compared with external preparations containing an adrenocortical hormone as a main active ingredient. Thus, external preparations useful in the treatment of various dermatoses can be obtained.

The external preparation for the treatment of dermatoses according to the fifth aspect of the present invention, which contains vitamin E, squalene and squalane, produces high therapeutic effects even on intractable dermatoses with reduced side effects as compared with external preparations containing an adrenocortical hormone as a main active ingredient. Therefore, external preparations useful in various dermatoses can be obtained. When the preparation vitamin E, squalene and squalane within respective specific concentration ranges, high therapeutic effects can be produced even against intractable dermatoses, with reduced side effects as compared with external preparations containing an adrenocortical hormone as a main active ingredient. Therefore, external preparations useful in the treatment of various dermatoses can be obtained. Furthermore, when said preparation further contains a specific transdermal absorption enhancer, the active ingredients can readily be adsorbed into the skin and high therapeutic effects can be produced even against intractable dermatoses, with reduced side effects as compared with external preparations containing an adrenocortical hormone as a main active ingredient. Thus, external preparations useful in the treatment of various dermatoses can be obtained.

What is claimed is:

1. An external preparation for the treatment of dermatoses which consists essentially of vitamin E and squalane, as main components, wherein the amount of vitamin E is about 20% by weight.

2. An external preparation for the treatment of dermatoses which consists essentially of vitamin E and squalane, as main components, wherein the amount of vitamin E is at least 20% by weight.

* * * * *